United States Patent
Kitano

(10) Patent No.: US 12,033,310 B2
(45) Date of Patent: Jul. 9, 2024

(54) IMAGE PROCESSING APPARATUS, RADIOSCOPY SYSTEM, IMAGE PROCESSING PROGRAM, AND IMAGE PROCESSING METHOD

(71) Applicant: FUJIFILM CORPORATION, Tokyo (JP)

(72) Inventor: Kouichi Kitano, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 224 days.

(21) Appl. No.: 17/322,820

(22) Filed: May 17, 2021

(65) Prior Publication Data

US 2021/0383514 A1 Dec. 9, 2021

(30) Foreign Application Priority Data

Jun. 5, 2020 (JP) ................................ 2020-098940

(51) Int. Cl.
*G06T 5/00* (2024.01)
*A61B 6/00* (2006.01)
(Continued)

(52) U.S. Cl.
CPC ................ *G06T 5/94* (2024.01); *A61B 6/025* (2013.01); *A61B 6/5211* (2013.01); *G06T 5/50* (2013.01);
(Continued)

(58) Field of Classification Search
None
See application file for complete search history.

(56) References Cited

U.S. PATENT DOCUMENTS

2013/0012813 A1\* 1/2013 Sakaguchi ............... A61B 6/12
600/431
2019/0046134 A1 2/2019 Imamura et al.
(Continued)

FOREIGN PATENT DOCUMENTS

JP 2011-139761 A 7/2011
JP 2015-526231 A 9/2015
(Continued)

OTHER PUBLICATIONS

English language translation of the following: Office action dated Apr. 25, 2023 from the JPO in a Japanese patent application No. 2020-098940 corresponding to the instant patent application. This office action translation is submitted now in order to supplement the understanding of the cited references which are being disclosed in the instant Information Disclosure Statement.

*Primary Examiner* — Hoon K Song
(74) *Attorney, Agent, or Firm* — SOLARIS Intellectual Property Group, PLLC

(57) ABSTRACT

An image processing apparatus includes at least one processor. The processor is configured to execute processing of acquiring a first image as a radiographic image including an image of a subject generated by radioscopy for continuously irradiating the subject with radiation to perform imaging, acquiring a second image different from the radiographic image including the image of the subject before acquiring the first image, specifying a subject region as a region where the image of the subject is formed in the first image, based on the second image, and executing image processing of enhancing contrast of the specified subject region on the first image and outputting the first image after the image processing.

8 Claims, 19 Drawing Sheets

(51) Int. Cl.
    *A61B 6/02*     (2006.01)
    *G06T 5/50*     (2006.01)
    *G06T 5/94*     (2024.01)

(52) U.S. Cl.
    CPC ............... *G06T 2207/10124* (2013.01); *G06T 2207/30004* (2013.01)

(56) References Cited

U.S. PATENT DOCUMENTS

2019/0046135 A1    2/2019   Hattori et al.
2020/0250824 A1*   8/2020   Yi .......................... G06T 7/0014

FOREIGN PATENT DOCUMENTS

| | | |
|---|---|---|
| JP | 2019033826 A | 3/2019 |
| JP | 2019033829 A | 3/2019 |
| JP | 2020074978 A | 5/2020 |

\* cited by examiner

IMAGE PROCESSING APPARATUS, RADIOSCOPY SYSTEM, IMAGE PROCESSING PROGRAM, AND IMAGE PROCESSING METHOD

CROSS-REFERENCE TO RELATED APPLICATIONS

The present application claims priority under 35 U.S.C. § 119 to Japanese Patent Application No. 2020-098940, filed on Jun. 5, 2020. The above application is hereby expressly incorporated by reference, in its entirety, into the present application.

BACKGROUND

1. Technical Field

A technique of the present disclosure relates to an image processing apparatus, a radioscopy system, an image processing program, and an image processing method.

2. Description of the Related Art

A technique is known in which a result of recognizing a subject of a radiographic image based on an image different from the radiographic image is used for control regarding imaging of the radiographic image. For example, JP2015-526231A describes a technique in which a collimation operation or the like in performing irradiation of an X-ray beam emitted from an X-ray source is controlled based on 3D image data of an object sensed by a sensor.

JP2011-139761A describes an X-ray diagnostic apparatus comprising an X-ray tube that generates X-rays, an X-ray detector that detects the X-rays generated from the X-ray tube and transmitted through a subject and outputs a signal corresponding to strength of the detected X-rays, a first camera that generates data of a first camera image regarding a front surface of the subject, an extraction unit that extracts the contour of the subject from the first camera image, a determination unit that determines whether or a time integral value of an in-contour signal corresponding to the inside of the contour of the subject among signal corresponding to the strength of the X-rays output from the X-ray detector reaches a threshold value set in advance, and an X-ray controller that stops the X-rays from the X-ray tube based on a result of determination by the determination unit.

SUMMARY

In a medical field, for example, a radioscopy apparatus is used in a case where examinations or operations, such as a gastric barium test, cystography, and orthopedic reduction, are performed. In radioscopy, a subject is continuously irradiated with radiation in a comparatively low dose from a radiation source, and accordingly, radiographic images (radioscopic images) continuously output from a radiation detector are displayed on a display in a form of video in real time.

For example, an operator who performs orthopedic reduction performs an operation for returning a dislocated joint of a patient to a normal state while observing the radioscopic image display on the display in real time. In this way, in a situation in which the operator performs an operation while observing the radioscopic image, in a case where the visibility of the radioscopic image displayed on the display is not satisfactory, it is considered that the operator hardly performs an operation for image quality adjustment. For example, automating contrast adjustment of the radioscopic image displayed on the display is automated makes it possible to eliminate a need for the operator performing the operation for image quality adjustment.

However, in a radioscopic image that is acquired in a situation in which there is a directly irradiated region as a region where irradiation of radiation is performed directly to the radiation detector without passing through the subject, there is a concern that contrast in a subject region decreases as affected by a pixel value in the directly irradiated region. Accordingly, it is considered that the subject region is specified by analyzing the acquired radioscopic image and the contrast of the specified subject region is enhanced; however, in this case, a comparatively long time is needed for specifying the subject region, and thus, a real time property in image display is damaged. In the radioscopy apparatus, the real time property of the image display is a particularly important element from a viewpoint of accurately performing an operation by the operator and from a viewpoint of suppressing an amount of exposure of the patient.

The technique of the present disclosure has been accomplished in view of the above-described point, and an object of the technique of the present disclosure is to increase visibility of a radiographic image while ensuring a real time property of image display.

The technique of the present disclosure provides an image processing apparatus comprising at least one processor. The processor is configured to execute processing of acquiring a first image as a radiographic image including an image of a subject generated by radioscopy for continuously irradiating the subject with radiation to perform imaging, acquiring a second image different from the radiographic image including the image of the subject before acquiring the first image, specifying a subject region as a region where the image of the subject is formed in the first image, based on the second image, and executing image processing of enhancing contrast of the specified subject region on the first image and outputting the first image after the image processing.

The second image may be a distance image indicating a distance to the subject. In this case, the processor may be configured to specify a region where the distance indicated by the distance image is within a predetermined range, as a region where the subject, and specify a region in the first image corresponding to the region specified as the region in the distance image where the subject is present, as the subject region in the first image. The distance image may be generated by a distance measurement camera that generates a distance image representing a distance to a surface of an object using a time-of-flight system.

The processor may be configured to acquire an updated second image at the time of non-irradiation of the radiation after the first image is acquired, update a specification result of the subject region in the first image based on the updated second image, and execute the image processing on the first image acquired after the acquisition of the updated second image based on the updated specification result.

The technique of the present disclosure provides a radioscopy system comprising the above-described image processing apparatus, a radiation detector that captures the first image, a radiation source that performs irradiation of radiation for use in imaging the first image, and an imaging apparatus that captures the second image.

The imaging apparatus may be a distance measurement camera that generates a distance image representing a distance to a surface of an object using a time-of-flight system.

The technique of the present disclosure provides an image processing program causing a processor in an image processing apparatus to execute processing of acquiring a first image as a radiographic image including an image of a subject generated by radioscopy for continuously irradiating the subject with radiation to perform imaging, acquiring a second image different from the radiographic image including the image of the subject before acquiring the first image, specifying a subject region as a region where the image of the subject is formed in the first image, based on the second image, and executing image processing of enhancing contrast of the specified subject region on the first image and outputting the first image after the image processing.

The technique of the present disclosure provides an image processing method in which a processor in an image processing apparatus executes processing of acquiring a first image as a radiographic image including an image of a subject generated by radioscopy for continuously irradiating the subject with radiation to perform imaging, acquiring a second image different from the radiographic image including the image of the subject before acquiring the first image, specifying a subject region as a region where the image of the subject is formed in the first image, based on the second image, and executing image processing of enhancing contrast of the specified subject region on the first image and outputting the first image after the image processing.

According to the technique of the present disclosure, it is possible to increase visibility of a radiographic image while ensuring a real time property of image display.

BRIEF DESCRIPTION OF THE DRAWINGS

FIG. 3A shows a manner in which the radiation generation unit is directed toward the left, and FIG. 3B shows a manner in which the radiation generation unit is directed toward the right.

Figure 14:
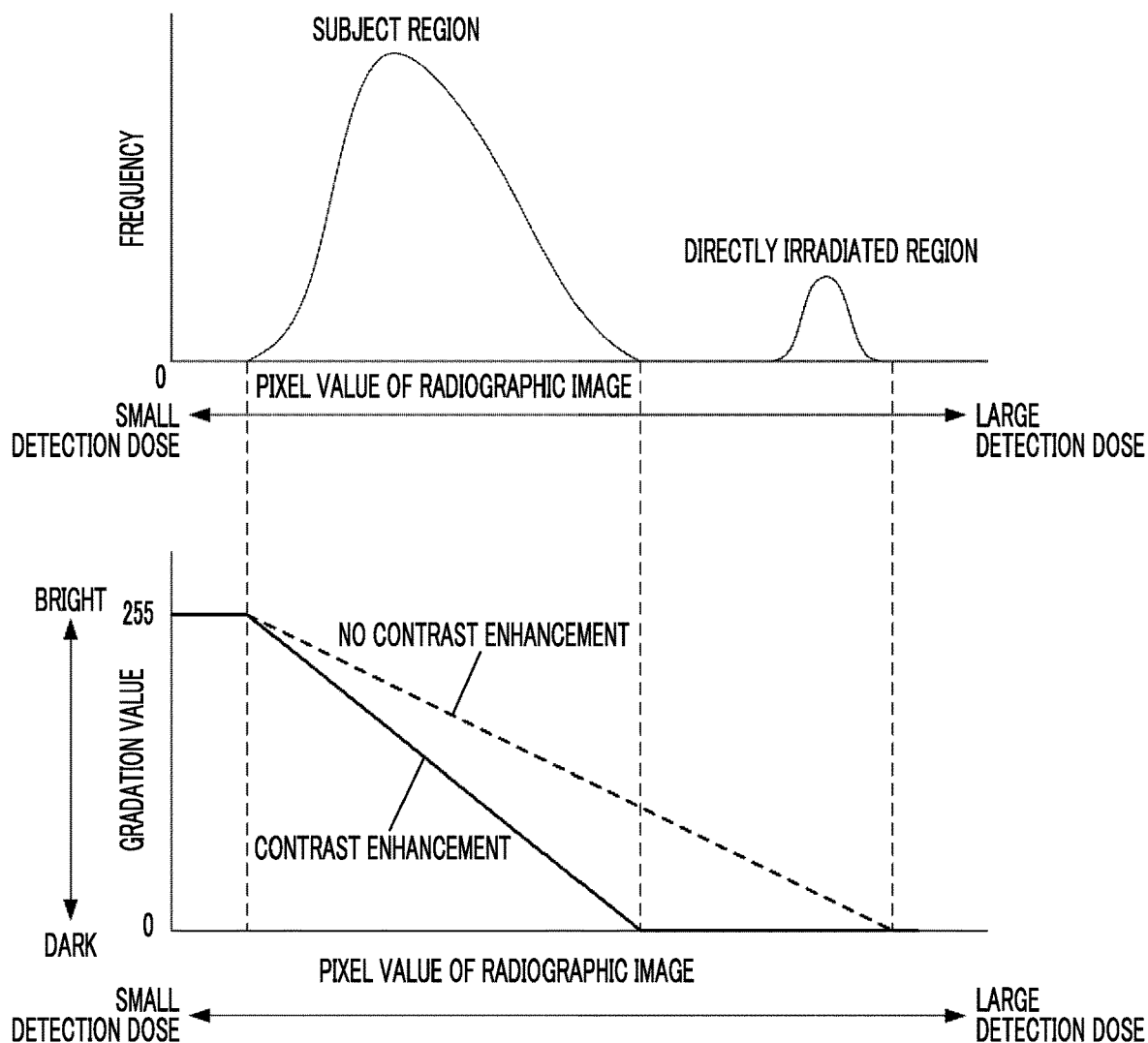

An upper section of FIG. 14 shows an example of a histogram of a pixel value of a radiographic image. A lower section of FIG. 14 is a diagram showing an example of image processing by an image processing unit, and is a diagram showing an example of a relationship between a pixel value of a radiographic image and a gradation value of a display image displayed on an operator monitor.

Figure 15:
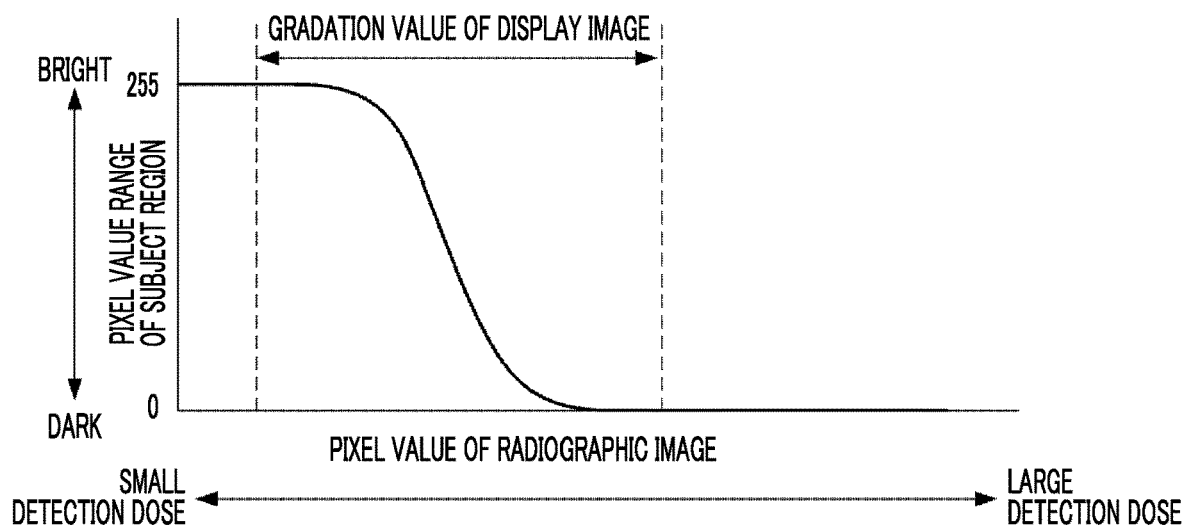

FIG. 15 is a diagram showing an example of the relationship between the pixel value of the radiographic image and the gradation value of the display image.

Figure 16:
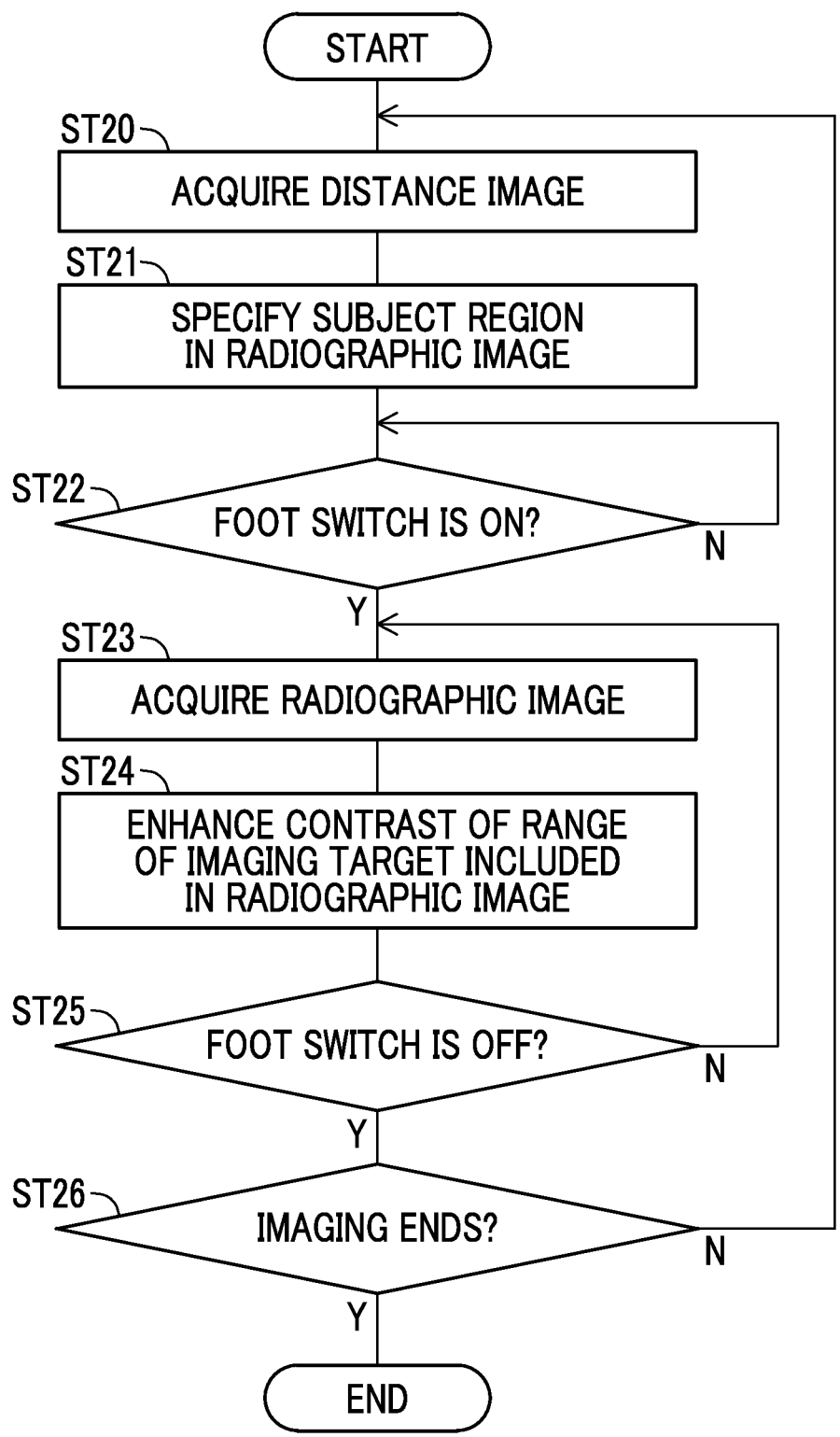

FIG. 16 is a flowchart showing an example of a flow of image processing that is executed by the CPU executing the image processing program.

Figure 17:
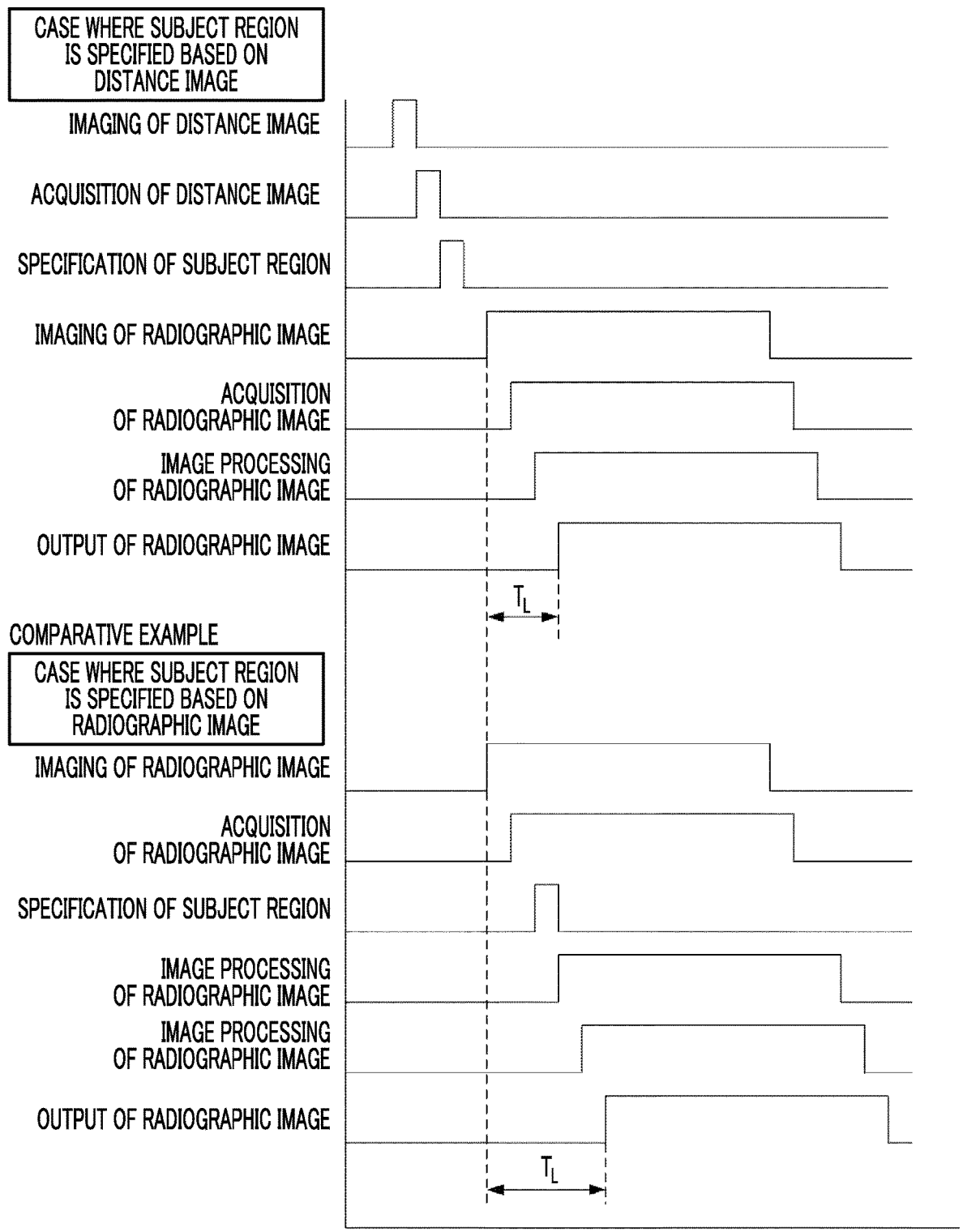

FIG. 17 is a timing chart showing an example of a flow of each kind of processing that is executed in a case of enhancing contrast of the subject region.

Figure 18:
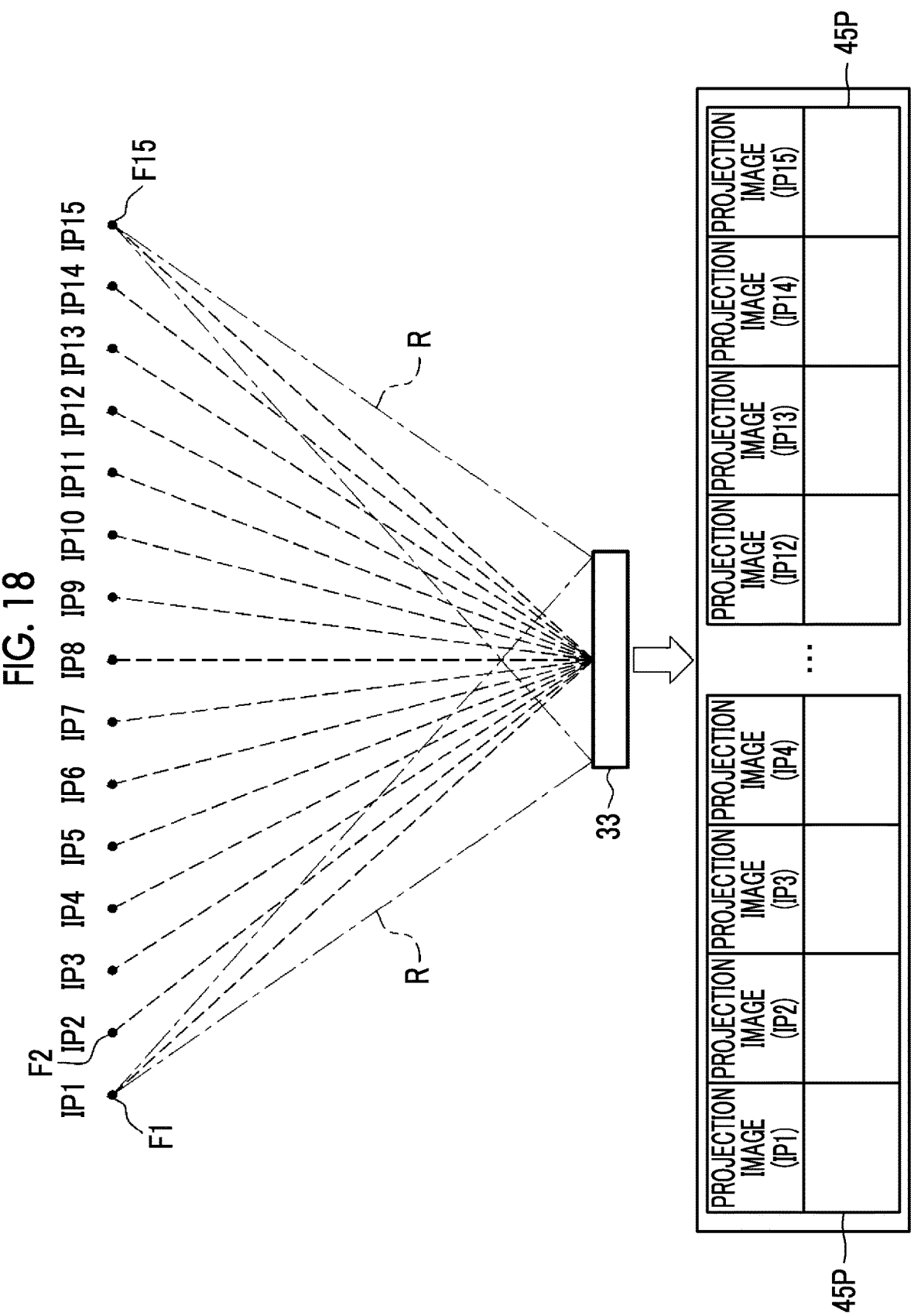

FIG. 18 is a diagram showing a manner of tomosynthesis imaging.

Figure 19:
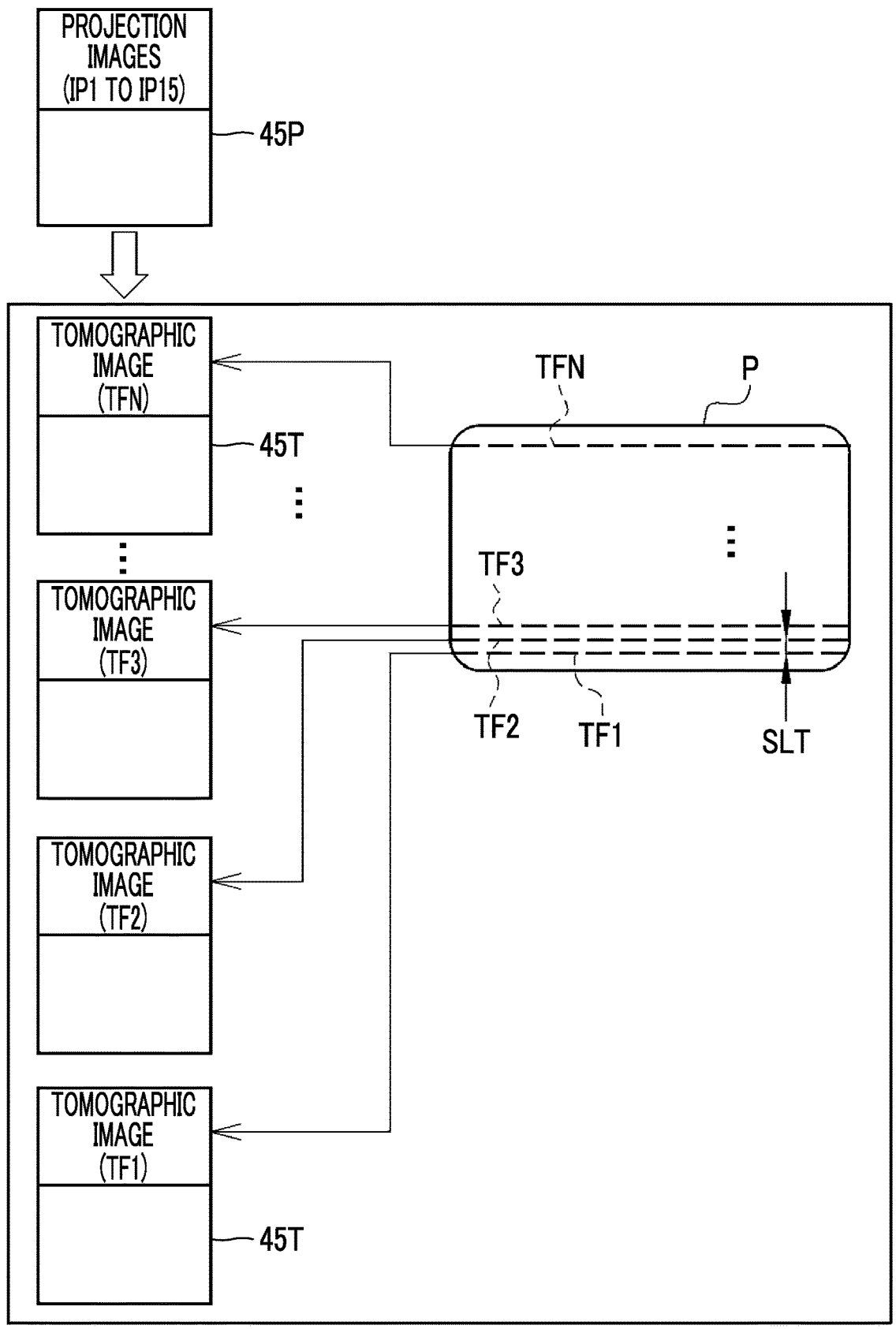

FIG. 19 is a diagram showing a manner of reconfiguring a tomographic image from a plurality of projection images obtained by tomosynthesis imaging.

Figure 20:
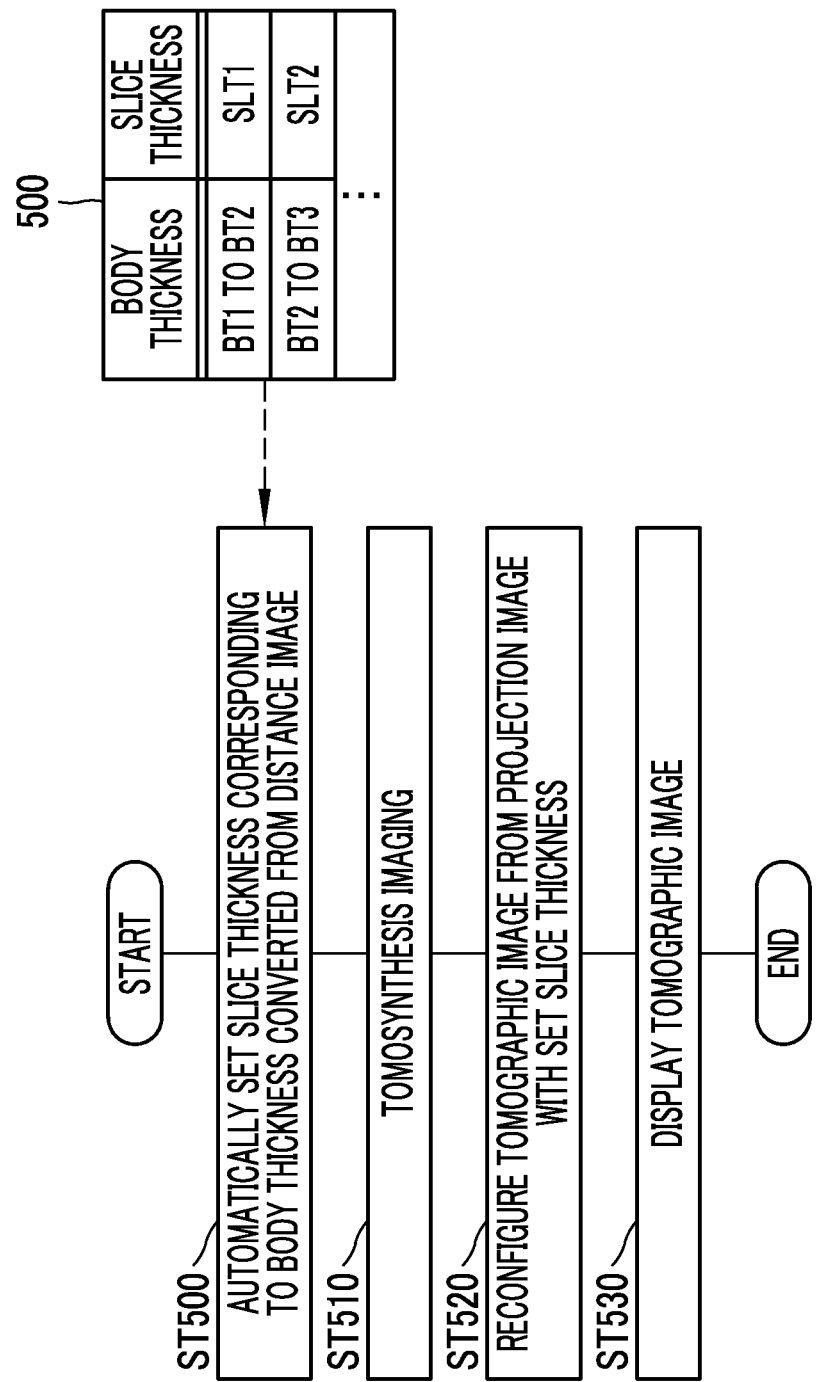

FIG. 20 is a flowchart showing an example of a procedure that is executed in reconfiguring a tomographic image.

Figure 21:
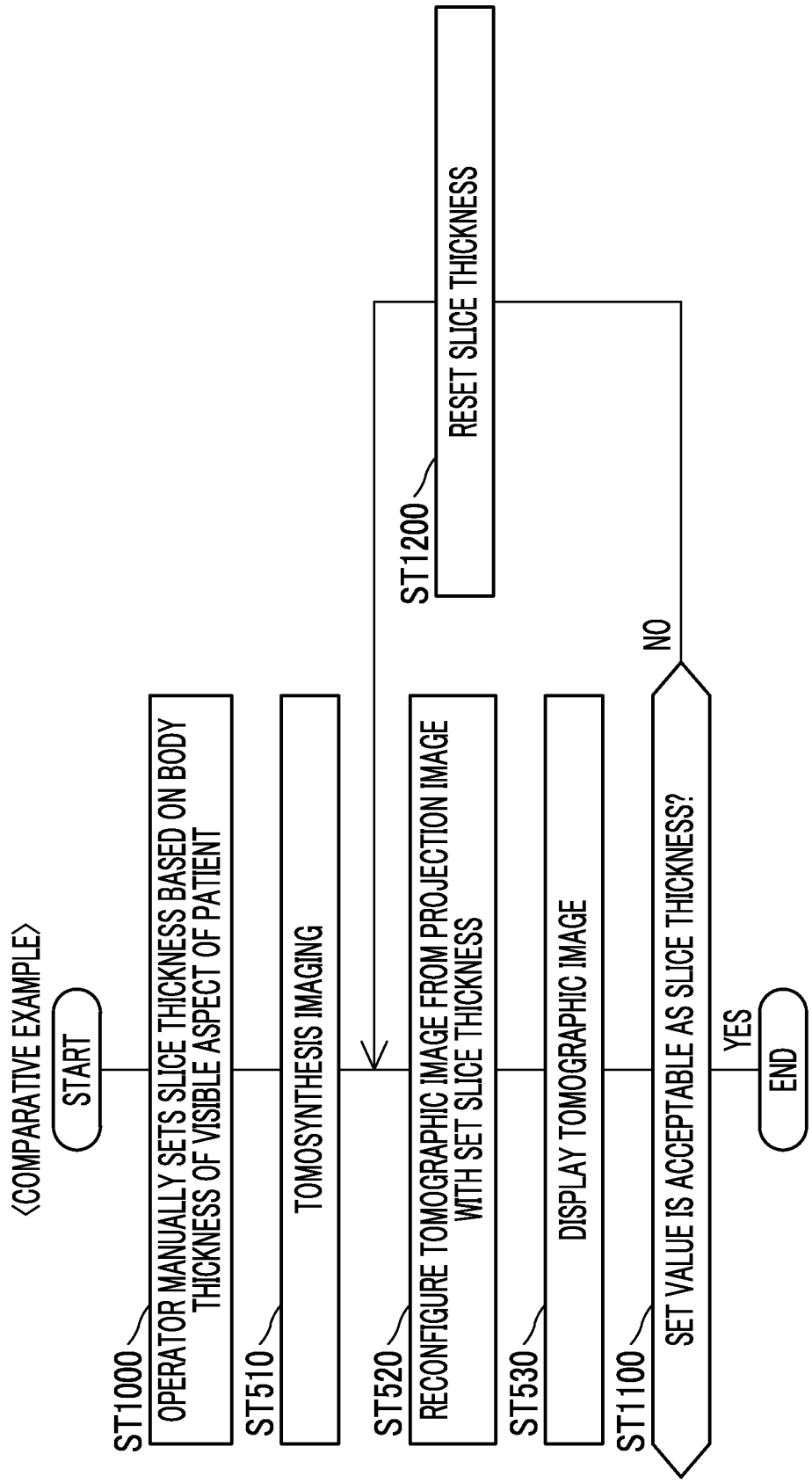

FIG. 21 is a flowchart showing an example of a procedure that is executed in reconfiguring a tomographic image.

DETAILED DESCRIPTION

Hereinafter, an example of an embodiment of the technique of the present disclosure will be described referring to the drawings. The same or equivalent components and portions in the respective drawings are represented by the same reference numerals, and overlapping description will not be repeated.

First Embodiment

Figure 1:
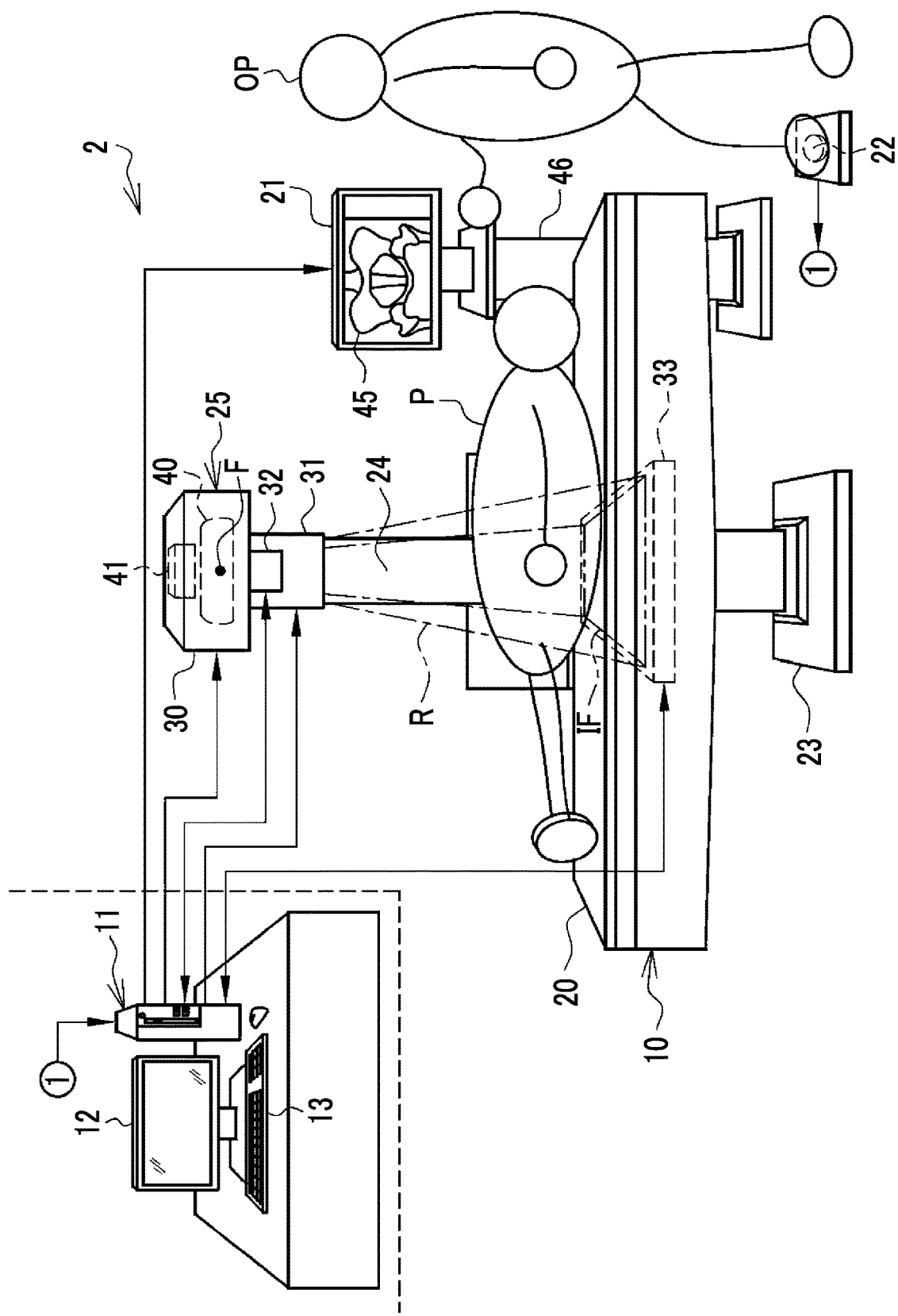
FIG. 1 is a diagram showing an example of a radioscopy system.

FIG. 1 is a diagram showing an example of the configuration of a radioscopy system 2 according to an embodiment of the technique of the present disclosure. The radioscopy system 2 comprises a radioscopy apparatus 10 and a console 11. The radioscopy apparatus 10 is provided in, for example, an operation room of a medical facility. The operation room is a room where an operator OP, such as a radiographer or a physician, performs an operation, such as a gastric barium test, cystography, or orthopedic reduction, to a patient P. The radioscopy apparatus 10 performs radioscopy to a patient P in operation. The patient P is an example of a "subject" in the technique of the present disclosure.

The console 11 is provided in, for example, a control room next to the operation room. The console 11 controls the operation of each unit of the radioscopy apparatus 10. The console 11 is, for example, a desktop personal computer, and has a display 12 and an input device 13, such as a keyboard or a mouse. The display 12 displays an imaging order or the like from a radiology information system (RIS). The input device 13 is operated by the operator OP in designating an imaging menu corresponding to the imaging order, or the like. The console 11 is an example of an "image processing apparatus" in the technique of the present disclosure.

The radioscopy apparatus 10 has an imaging table 20, an operator monitor 21, a foot switch 22, and the like. The imaging table 20 is supported on a floor surface of the operation room by a stand 23. A radiation generation unit 25 is attached to the imaging table 20 through a post 24. The radiation generation unit 25 includes a radiation source 30, a collimator 31, and a distance measurement camera 32. A radiation detector 33 is incorporated in the imaging table 20.

The radiation source 30 has a radiation tube 40. The radiation tube 40 emits radiation R, such as X-rays or γ-rays, and irradiates the patient P lying on the imaging table 20 with the radiation R, for example. The radiation tube 40 is provided with a filament, a target, a grid electrode, and the like (all are not shown). A voltage is applied between the filament as a cathode and the target as an anode from a voltage generator 41. The voltage that is applied between the filament and the target is referred to as a tube voltage. The filament discharges thermoelectrons according to the applied tube voltage toward the target. The target radiates the radiation R with collision of the thermoelectrons from the filament. The grid electrode is disposed between the filament and the target. The grid electrode changes a flow rate of the thermoelectrons from the filament toward the target depending on the voltage applied from the voltage generator 41. The flow rate of the thermoelectrons from the filament toward the target is referred to as a tube current. The tube voltage and the tube current are set as irradiation conditions (see FIG. 7) along with an irradiation time.

The collimator 31 and the distance measurement camera 32 are attached to a lower portion of the radiation source 30. The collimator 31 limits an irradiation field IF of the radiation R generated from the radiation tube 40. For example, the collimator 31 has a configuration in which four shield plates formed of lead or the like shielding the radiation R are disposed on respective sides of a quadrangle, and an emission opening of the quadrangle transmitting the radiation R is formed in a center portion. The collimator 31 changes the positions of the shield plates to change an opening degree of the emission opening, and accordingly, changes the irradiation field IF.

The distance measurement camera 32 is a camera that measures a distance to an object surface using a time-of-flight (TOF) system. The distance measurement camera 32 is viewed to be substantially as the same position as the radiation source 30, more exactly, a focus F of the radiation tube 40 at which the radiation R is generated, as viewed from the patient P side. For this reason, the distance measurement camera 32 may measure a distance between the radiation source 30 and an object surface. The object surface may be, for example, a body surface of the patient P or a surface of the imaging table 20. A distance between the focus F and the distance measurement camera 32 may be measured in advance, and a result obtained by adding the distance measured in advance between the focus F and the distance measurement camera 32 to the distance measured by the distance measurement camera 32 may be set as the distance between the radiation source 30 and the object surface. In the example, the distance between the radiation source 30 and the surface of the imaging table 20 is invariable. The distance measurement camera 32 is an example of an "imaging apparatus" in the technique of the present disclosure.

The radiation detector 33 has a configuration in which a plurality of pixels that are sensitive to the radiation R or visible light converted from the radiation R by a scintillator to generate signal charge are arranged. Such a radiation detector 33 is referred to as a flat panel detector (FPD). The radiation detector 33 detects the radiation R emitted from the radiation tube 40 and transmitted through the patient P, and outputs a radiographic image 45. The radiation detector 33 transmits the radiographic image 45 to the console 11. A series of radiographic images 45 that are continuously captured by continuously performing the irradiation of the radiation R from the radiation source 30 are also referred to as radioscopic images. The radiographic image 45 is an example of a "first image" in the technique of the present disclosure.

The operator monitor 21 is supported on the floor surface of the operation room by a stand 46. The radiographic image 45 that is output from the radiation detector 33 and is subjected to various kinds of image processing with the console 11 is displayed on the operator monitor 21 in a form of video in real time.

The foot switch 22 is a switch for the operator OP giving an instruction to start and end radioscopy while being seated in the operation room. In a case where the operator OP depresses the foot switch 22 with a foot (on state), radioscopy is started. Then, while the operator OP is depressing the foot switch 22 with the foot, the irradiation of the radiation R is continuously performed, and radioscopy is continued. In a case where the operator OP releases the foot from the foot switch 22, and the depression of the foot switch 22 is released (off state), a non-irradiation state of the radiation R is brought, and radioscopy ends.

Figure 2:
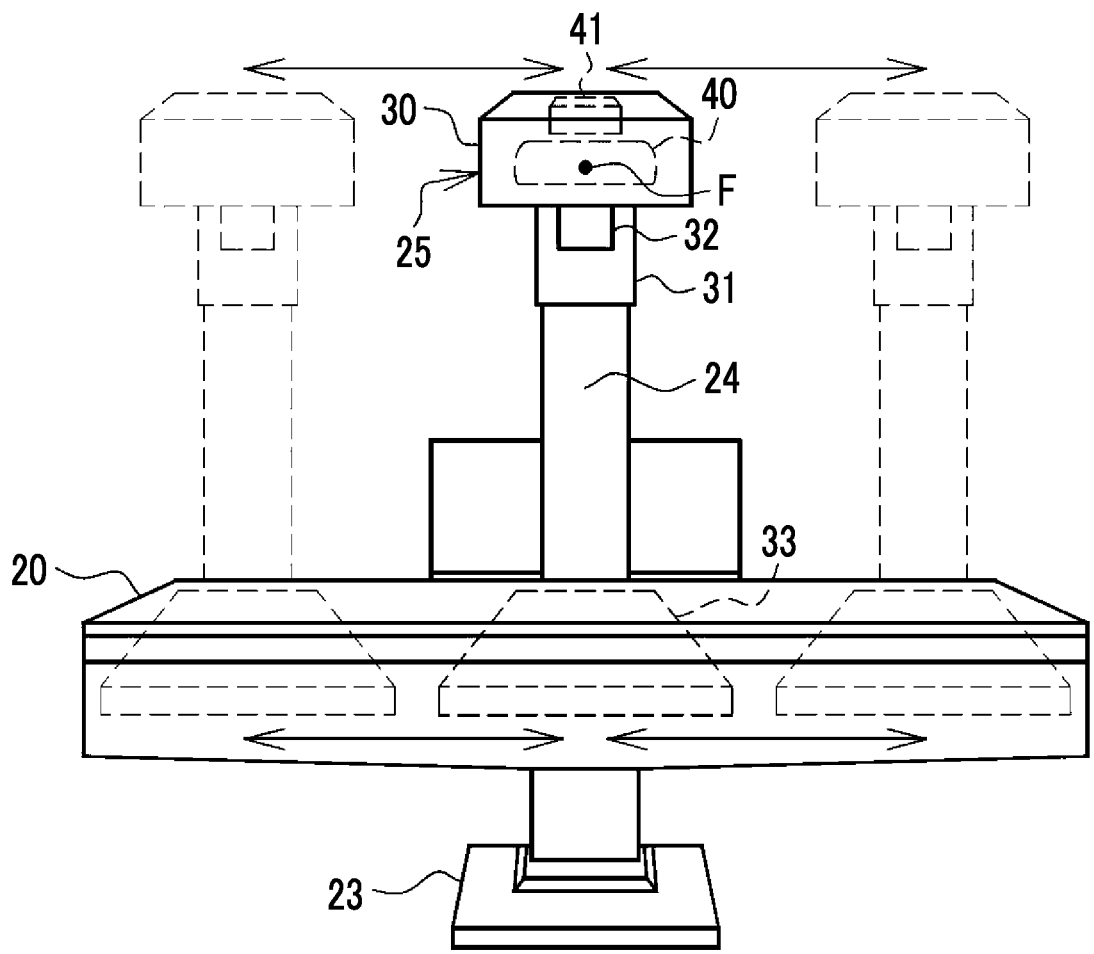
FIG. 2 is a diagram showing a manner in which a radiation generation unit and a radiation detector reciprocate along a longitudinal direction of an imaging table.

As shown in FIG. 2, the radiation generation unit 25 can reciprocate along a longitudinal direction of the imaging table 20 along with the post 24 by a movement mechanism (not shown). The radiation detector 33 can also reciprocate along the longitudinal direction of the imaging table 20 in conjunction with the movement of the radiation generation unit 25. The radiation detector 33 is moved to a position where the center thereof confronts the focus F of the radiation tube 40. The imaging table 20 is provided with a control panel (not shown) for inputting an instruction to move the radiation generation unit 25 and the radiation detector 33. The operator OP inputs an instruction through the control panel and moves the radiation generation unit 25 and the radiation detector 33 to desired positions. The radiation generation unit 25 and the radiation detector 33 can be controlled by remote control by a control console (not shown) from the control room.

Figure 3A:
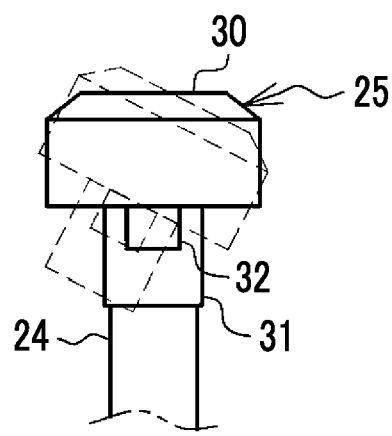
FIGS. 3A and 3B are diagrams showing a manner in which an angle of the radiation generation unit is changed.
Figure 3B:
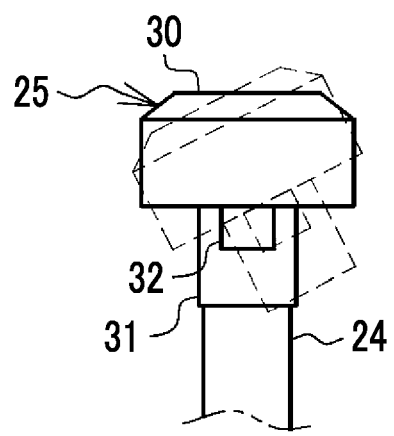

As shown in FIGS. 3A and 3B, the radiation generation unit 25 can change an angle right and left with respect to the post 24 with a hand of the operator OP. A changeable maximum angle is, for example, 90° right and left. The changing of the angle of the radiation generation unit 25 with respect to the post 24 can be controlled by remote control from the control room.

Figure 4:
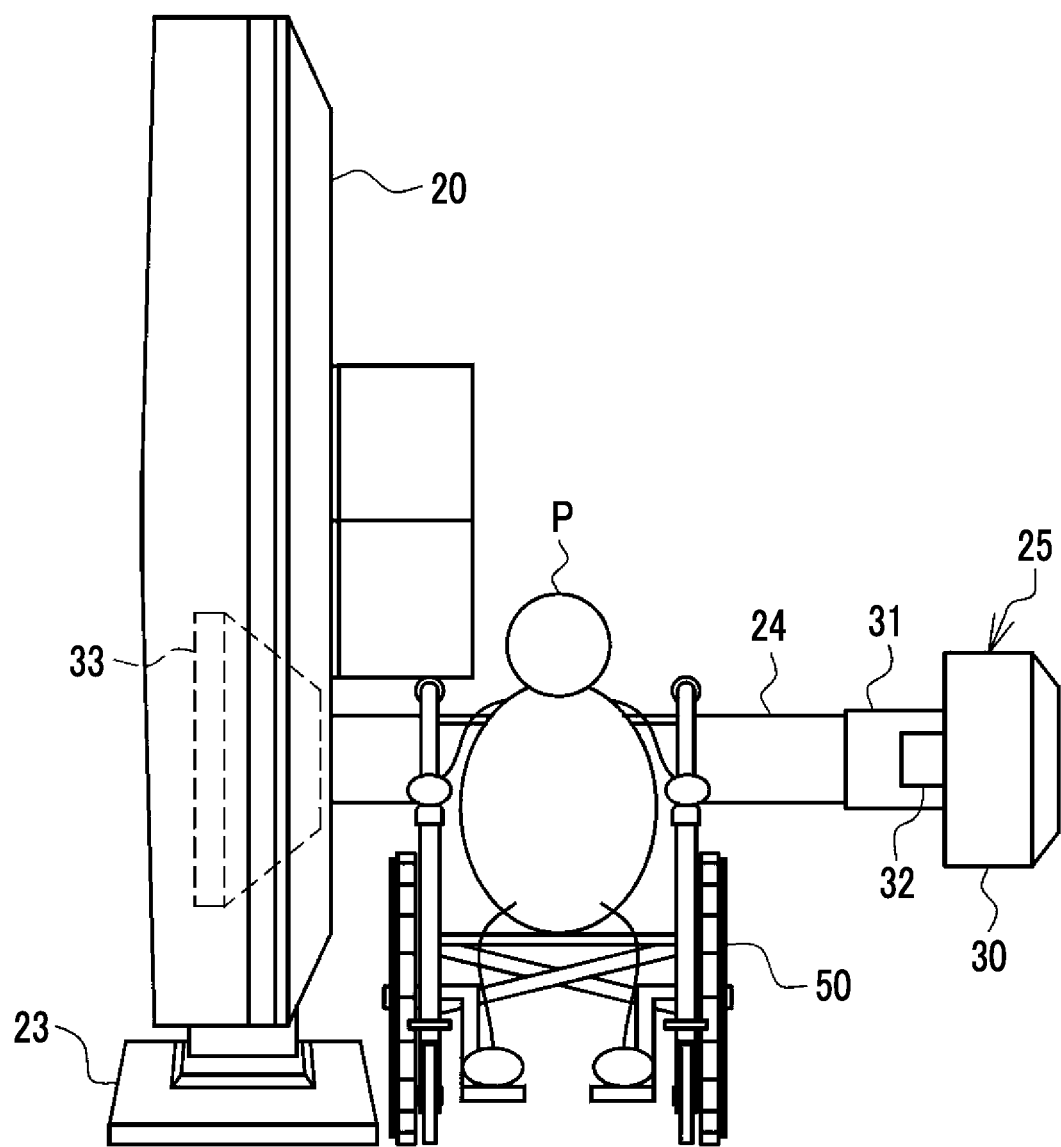
FIG. 4 is a diagram showing a manner in which radioscopy is performed on a patient in a wheelchair with an imaging table and a post in an upright state.
Figure 5:
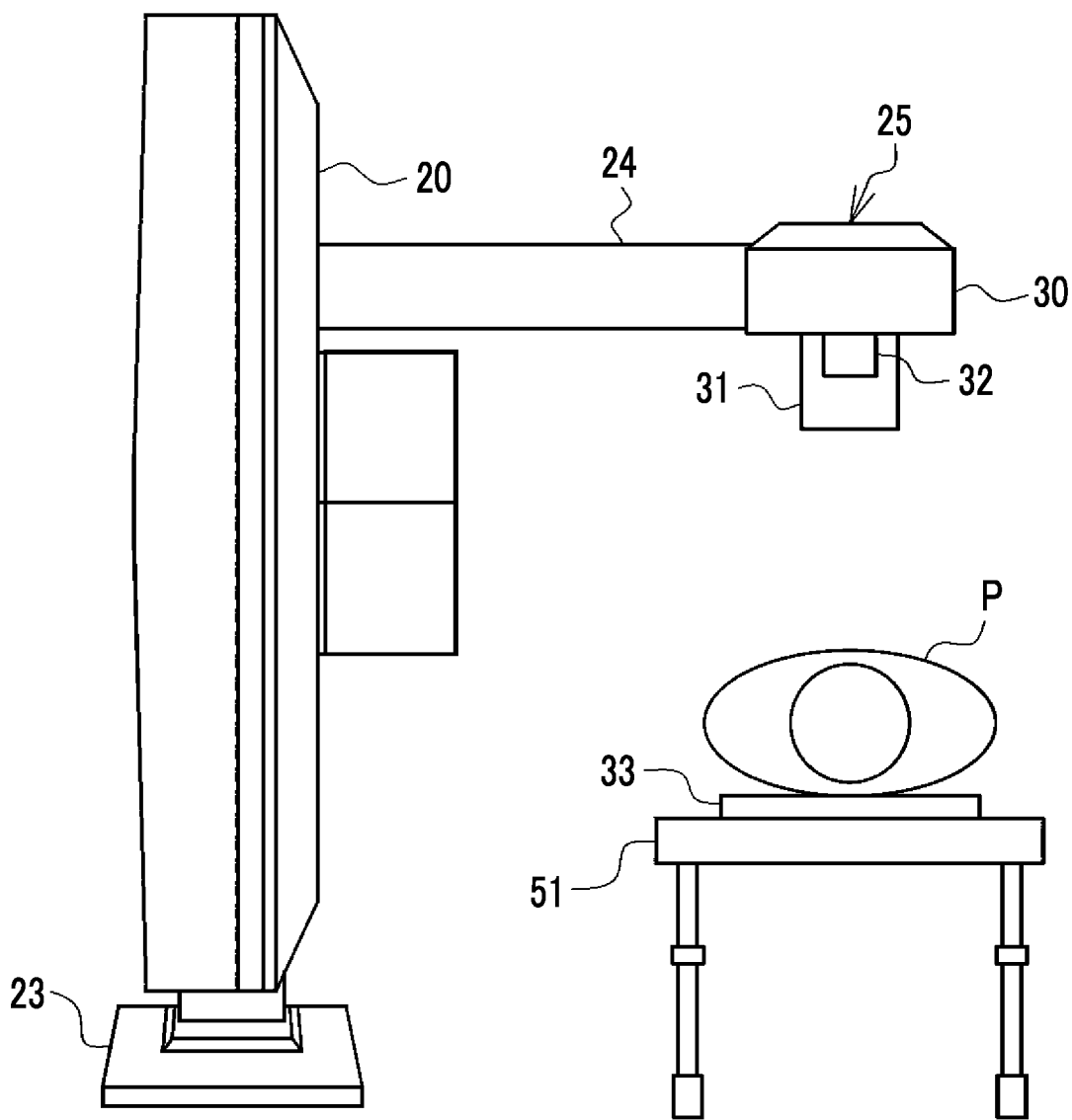
FIG. 5 is a diagram showing a manner in which radioscopy is performed on a patient on a stretcher with the imaging table and the post in the upright state.

The imaging table 20 and the post 24 can rotate between a decubitus state shown in FIGS. 1 and 2 and an upright state shown in FIGS. 4 and 5 by a rotation mechanism (not shown), such as a motor. The decubitus state is a state in which the surface of the imaging table 20 is parallel to the floor surface and the post 24 is perpendicular to the floor surface. On the other hand, the upright state is a state in which the surface of the imaging table 20 is perpendicular to the floor surface, and the post 24 is parallel to the floor surface. In the upright state, not only radioscopy on the patient P in an upright posture, but also radioscopy on the patient P in a wheelchair 50 as shown in FIG. 4 can be performed. In the upright state, radioscopy on the patient P on a stretcher 51 as shown in FIG. 5 can also be performed. In the case of FIG. 5, the radiation detector 33 is detached from the imaging table 20 and is set between the patient P and the stretcher 51.

Figure 6:
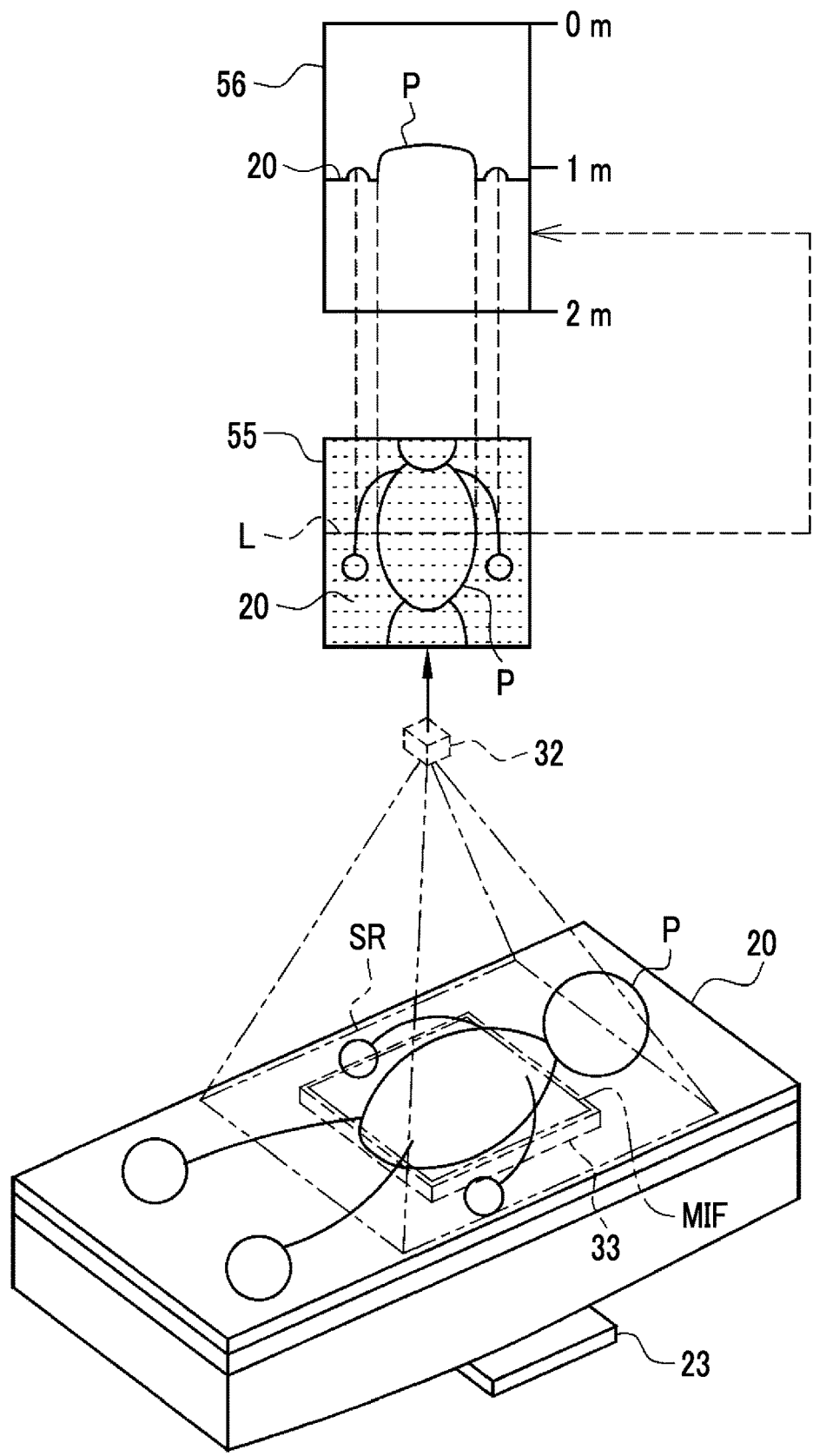
FIG. 6 is a diagram showing a manner in which the patient and the periphery of the patient are imaged with a distance measurement camera and a distance image representing a distance between a radiation source and an object surface is output.

As shown in FIG. 6, the distance measurement camera 32 images a rectangular imaging range SR including the patient P and the periphery of the patient P, and outputs a distance image 55. The imaging range SR of the distance measurement camera 32 is a range sufficiently wider than a maximum irradiation field MIF of the radiation R, and covers the entire maximum irradiation field MIF of the radiation R.

The distance image 55 is an image that represents a distance between the radiation source 30 and an object surface with an attachment position of the distance measurement camera 32, that is, a position of the radiation source 30 as 0 m, as illustrated with a profile 56 of a line L at the center. The distance image 55 has the distance between the radiation source 30 and the surface of the object in the imaging range SR including the patient P and the imaging table 20 as a pixel value of each pixel. The distance image 55 is an example of a "second image" in the technique of the present disclosure.

Figure 7:
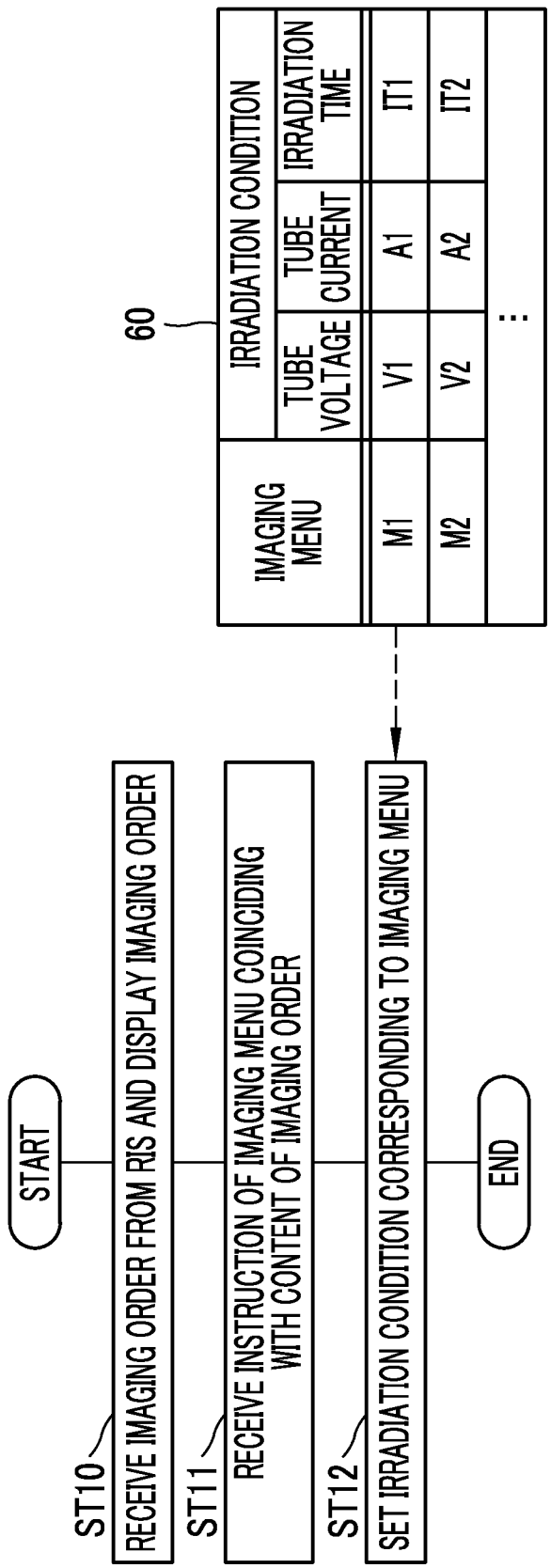
FIG. 7 is a flowchart showing a procedure for setting irradiation conditions.

FIG. 7 is a flowchart showing an example of a procedure for setting the irradiation conditions of the radiation R in a case where radioscopy is performed. As shown in FIG. 7, prior to radioscopy, the console 11 receives the imaging order from the RIS and displays the imaging order on the display 12 (Step ST10). In the imaging order, patient identification data (ID) for identifying the patient P, an instruction of an operation by a physician of a treatment department who issues the imaging order, and the like are registered. The operator OP confirms the content of the imaging order through the display 12.

The console 11 displays a plurality of kinds of imaging menus prepared in advance on the display 12 in an alternatively selectable form. The operator OP selects one imaging menu corresponding to the content of the imaging order through the input device 13. With this, the console 11 receives a selection instruction of the imaging menu (Step ST11). The console 11 sets the irradiation conditions corresponding to the selection-instructed imaging menu with reference to an irradiation condition table 60 (Step ST12). After selecting the imaging menu, the operator OP performs positioning and the like of the radiation source 30, the radiation detector 33, and the patient P, and depresses the foot switch 22 with the foot to start radioscopy. The irradiation conditions have content where the irradiation of the radiation R is performed with an extremely low dose compared to a case where general radiography is performed.

Figure 8:
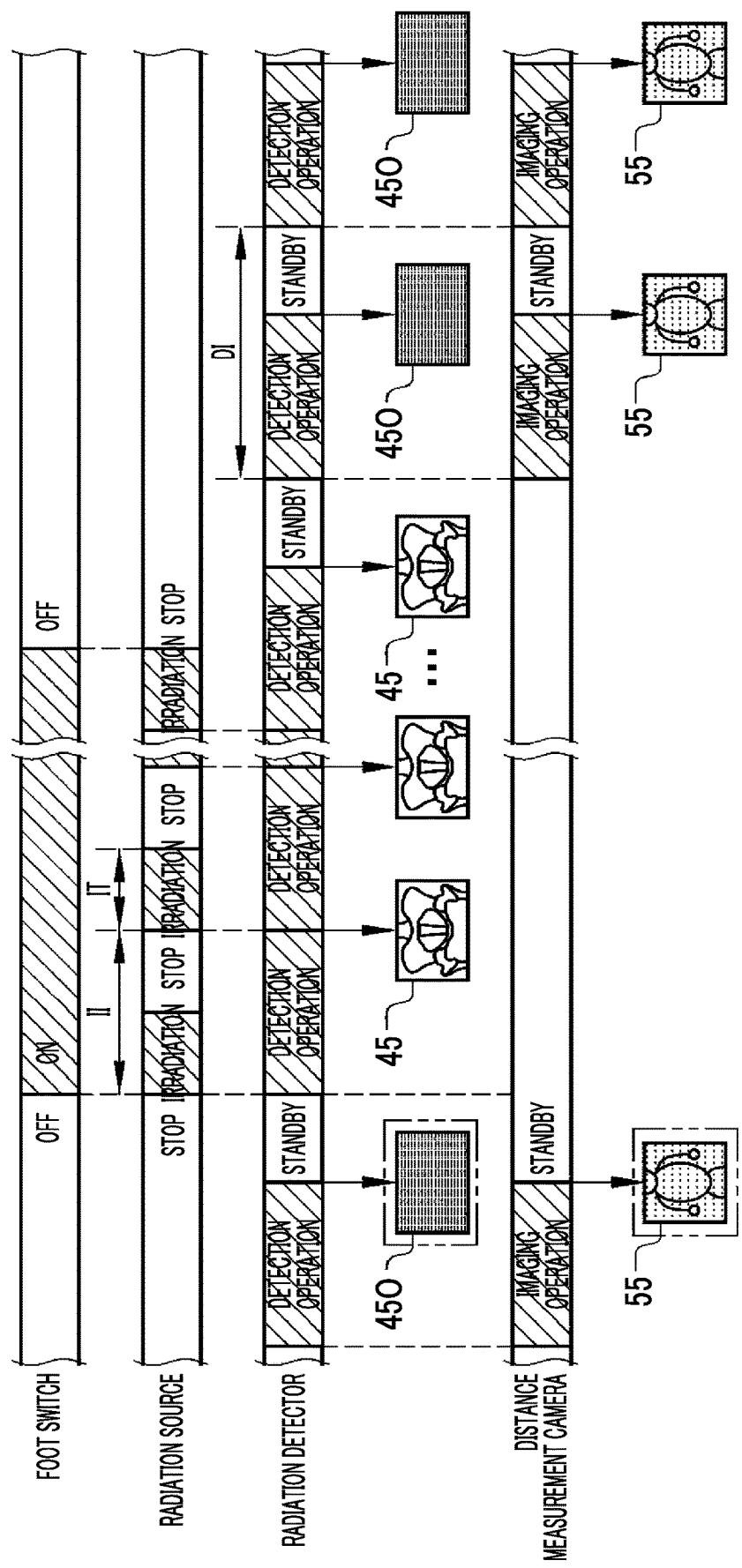
FIG. 8 is a timing chart showing an operation timing of each unit in radioscopy.

FIG. 8 is a timing chart showing an example of an operation timing of each unit in radioscopy. As shown in FIG. 8, the radiation source 30 starts the irradiation of the radiation R under the set irradiation conditions in synchronization with a timing at which the foot switch 22 is depressed, that is, a timing from foot switch-off to foot switch-on in the drawing. The radiation source 30 repeats the irradiation and the stop of the radiation R at an irradiation interval II set in advance while the foot switch 22 is being depressed. That is, the radiation source 30 continuously irradiates the patient P with the radiation R. The radiation source 30 stops the irradiation of the radiation R in a case where the depression of the foot switch 22 is released. The irradiation interval II is variable with about 0.033 seconds (30 frames per second (fps) as converted into a frame rate) as an upper limit. A reference sign IT indicates an irradiation time set under the irradiation conditions.

The radiation detector 33 starts a detection operation in synchronization with an irradiation start timing of the radiation R. The radiation detector 33 repeats the detection operation while the foot switch 22 is being depressed, and the irradiation of the radiation R is being performed from the radiation source 30 in a pulsed manner. With the repetitive detection operation during the irradiation of the radiation R, the radiation detector 33 outputs the radiographic image 45 at the same interval as the irradiation interval II. The radiation detector 33 transmits the radiographic image 45 to the console 11.

The radiation detector 33 also performs the detection operation in a non-irradiation period of the radiation R before the foot switch 22 is depressed and before the depression of the foot switch 22 is released. The radiation detector 33 repeatedly performs the detection operation in advance in the non-irradiation period of the radiation R at a detection interval DI set. The detection interval DI is a time sufficiently longer than the irradiation interval II of the radiation R, and is, for example, one minute. With the detection operation in a state in which the irradiation of the radiation R is not performed, the radiation detector 33 outputs an offset correction radiographic image (hereinafter, referred to as an offset correction image) 45O. The radiation detector 33 transmits the offset correction image 45O to the console 11.

The distance measurement camera 32 performs an imaging operation of the distance image 55 in synchronization with the detection operation of the offset correction image 45O of the radiation detector 33 in the non-irradiation period of the radiation R before the foot switch 22 is depressed and before the depression of the foot switch 22 is released.

In FIG. 8, although an aspect where the irradiation of the radiation R is performed in a pulsed manner has been exemplified, the present disclosure is not limited thereto. An aspect where the irradiation of the radiation is consecutively performed while the foot switch 22 is being depressed with the foot of the operator OP may be employed. Even in an aspect where the irradiation of the radiation R is performed in a pulsed manner or an aspect where the irradiation of the radiation R is consecutively performed, the fact remains that the patient P is continuously irradiated with the radiation R.

Figure 9:
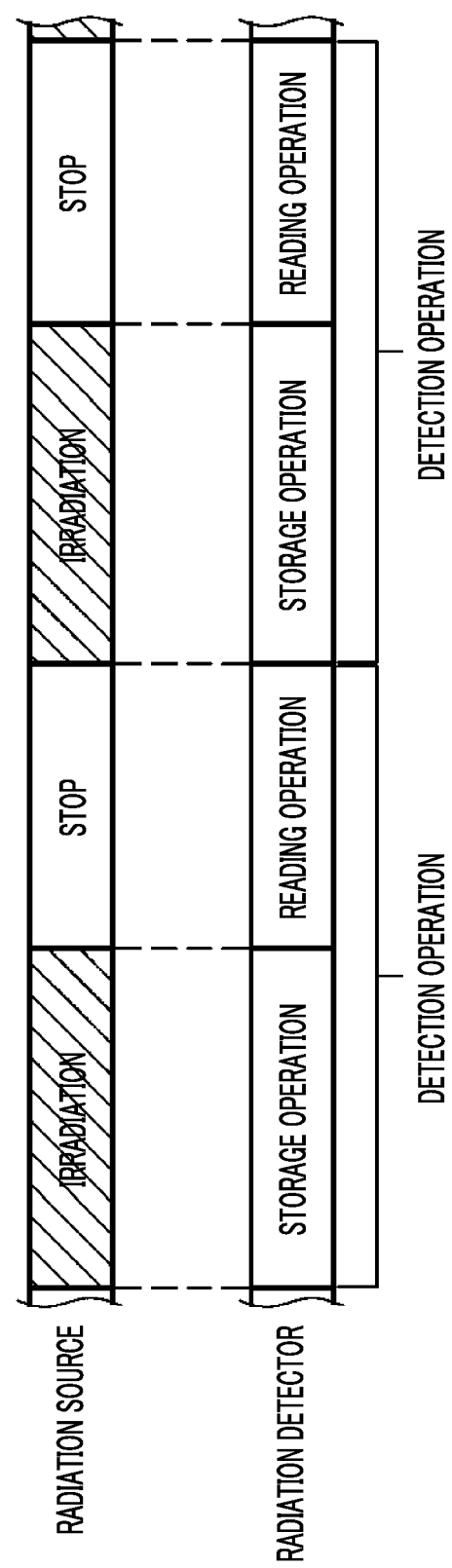
FIG. 9 is a timing chart showing specific content of a detection operation.

FIG. 9 is a timing chart showing an example of specific content of the detection operation in the radiation detector 33. As shown in FIG. 9, the detection operation is constituted of a storage operation and a reading operation. The storage operation is an operation to store signal charge in a pixel, and is started in synchronization with the irradiation start timing of the radiation R. The reading operation is an operation to read the signal charge stored in the pixel and to output the signal charge as the radiographic image 45, and is started in synchronization with an irradiation end timing of the radiation R.

Figure 10:
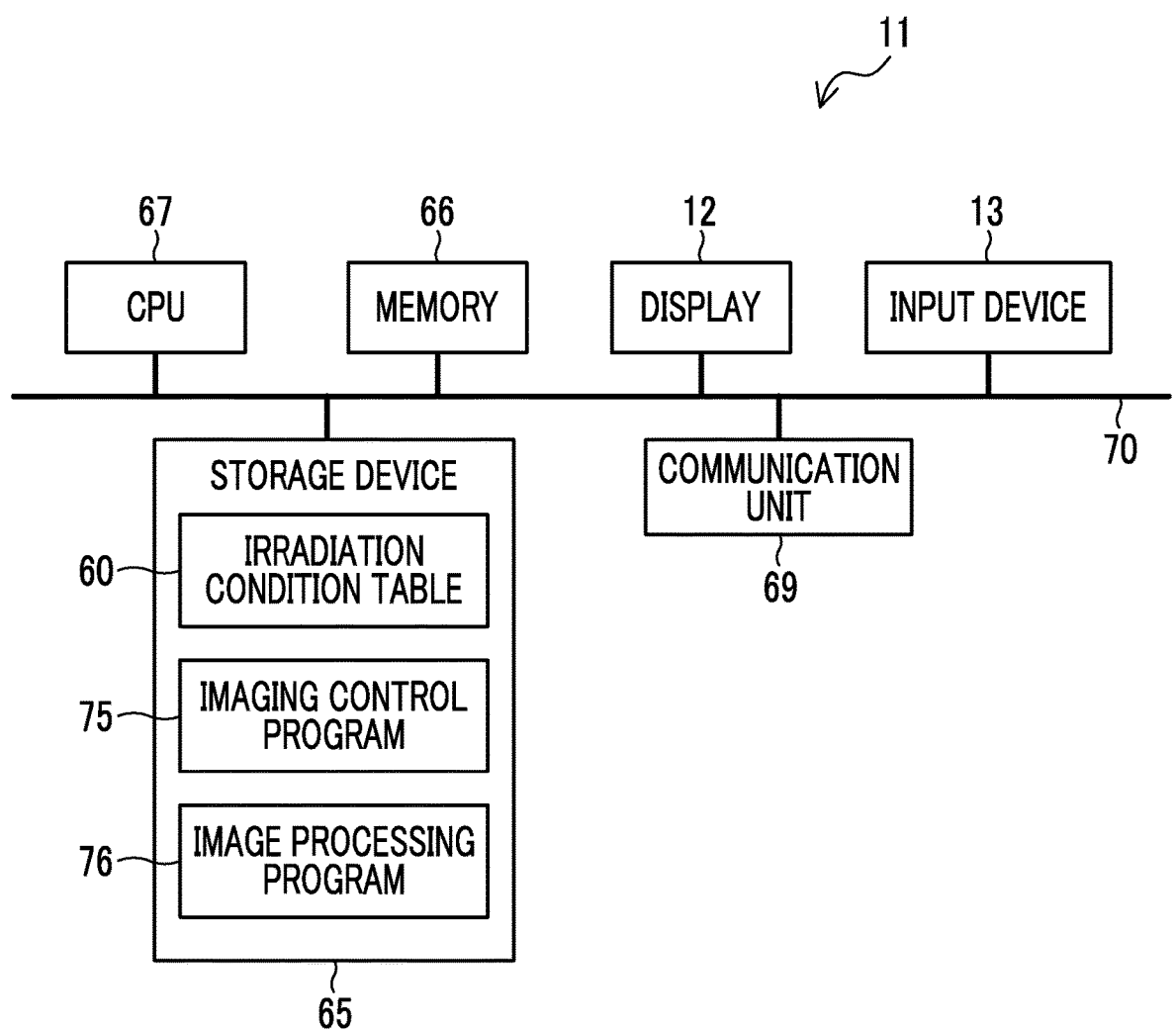
FIG. 10 is a diagram showing an example of the hardware configuration of a console.

FIG. 10 is a diagram showing an example of the hardware configuration of the console 11. The console 11 comprises a central processing unit (CPU) 67, a memory 66 as a temporary storage area, a nonvolatile storage device 65, and a communication unit 69 that takes charge of communication of various kinds of information with each unit of the radioscopy apparatus 10, in addition to the display 12 and the input device 13 described above. Such hardware components constituting the console 11 are connected to one another through a busline 70.

The storage device 65 is realized by a storage medium, such as a hard disk drive (HDD), a solid state drive (SSD), or a flash memory. In the storage device 65, an imaging control program 75, an image processing program 76, and the irradiation condition table 60 are stored. The CPU 67 reads the imaging control program 75 and the image processing program 76 from the storage device 65, develops the imaging control program 75 and the image processing program 76 to the memory 66, and executes the imaging control program 75 and the image processing program 76 based on an execution instruction input using the input device 13. The CPU 67 is an example of a "processor" in the technique of the present disclosure.

Figure 11:
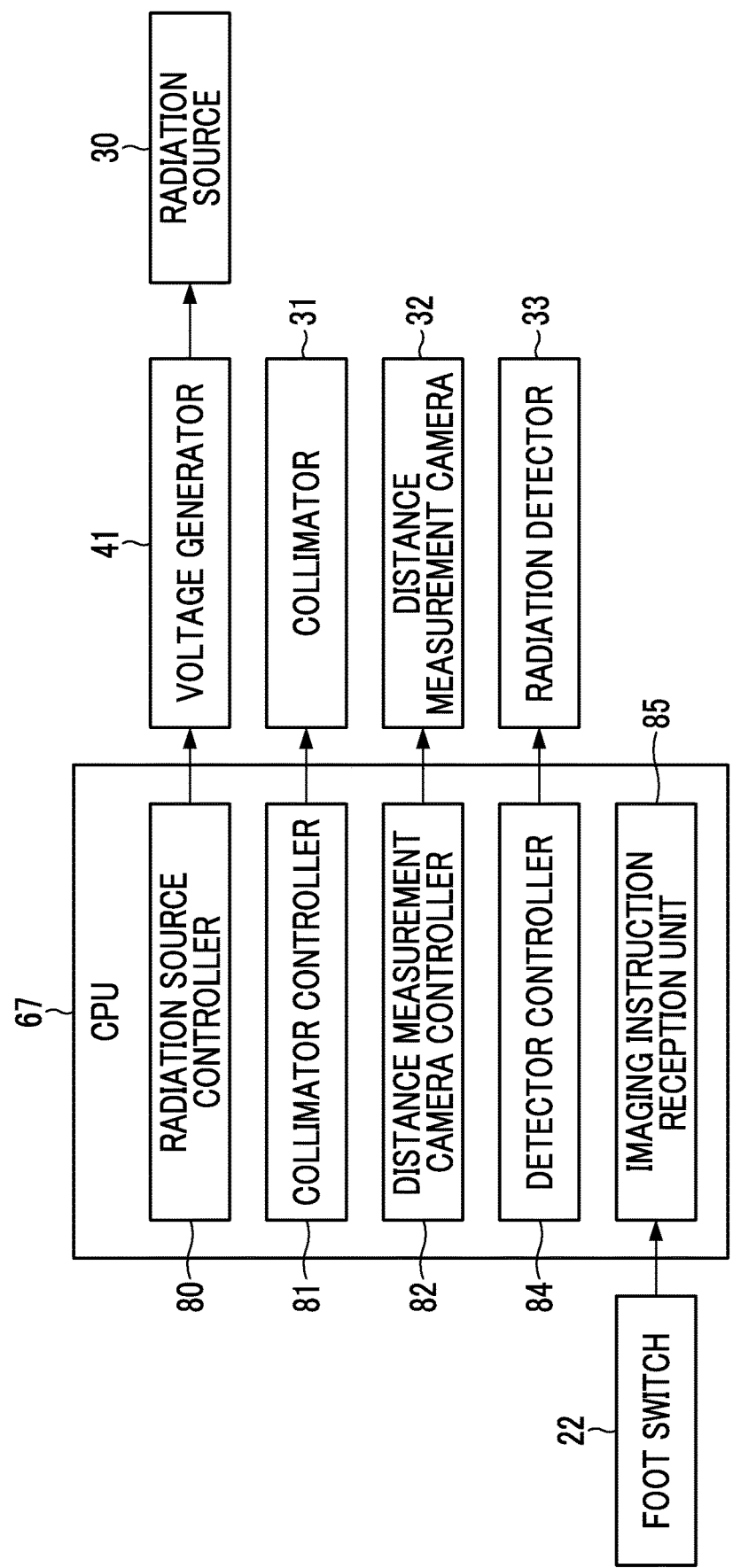
FIG. 11 is a block diagram showing an example of the functional configuration of a CPU that executes an imaging control program.

FIG. 11 is a block diagram showing an example of the functional configuration of the CPU 67 that executes the imaging control program 75. As shown in FIG. 11, the CPU 67 functions as a radiation source controller 80, a collimator controller 81, a distance measurement camera controller 82, a detector controller 84, and an imaging instruction reception unit 85 by executing the imaging control program 75.

The radiation source controller 80 controls the operation of the radiation source 30 to control the irradiation of the radiation R. The radiation source controller 80 reads the irradiation conditions corresponding to the imaging menu selected by the operator OP from the irradiation condition table 60, and sets the tube voltage corresponding to the read irradiation conditions in the voltage generator 41. The radiation source controller 80 causes the irradiation of the radiation R from the radiation source 30 through the voltage generator 41 under the set irradiation conditions. The radiation source controller 80 outputs irradiation start and stop timings of the radiation R to the detector controller 84.

The radiation source controller 80 performs auto brightness control (ABC). As known in the art, the ABC is feedback control where, to maintain the brightness of the radiographic image 45 within a given range, during radioscopy, the tube voltage, the tube current, the irradiation time IT, the irradiation interval II, and the like given to the radiation tube 40 are finely adjusted based on a brightness value (for example, an average value of brightness values of a center region of the radiographic image 45) of the radiographic image 45 sequentially output from the radiation detector 33. With the ABC, degradation of the visibility of the radiographic image 45 due to extreme change in brightness of the radiographic image 45 caused by body movement or the like of the patient P is suppressed.

The collimator controller 81 controls the operation of the shield plates of the collimator 31 and adjusts the opening degree of the emission opening formed by the shield plates to an opening degree corresponding to the imaging menu selected by the operator OP. The opening degree of the emission opening can also be adjusted by the operator OP through a control panel (not shown) provided in the collimator 31 itself.

The distance measurement camera controller 82 controls the operation of the distance measurement camera 32. Specifically, the distance measurement camera controller 82 makes the distance measurement camera 32 perform an imaging operation of the distance image 55 in synchronization with the timing at which the radiation detector 33 outputs the offset correction image 45O in a case where the irradiation of the radiation R is not performed.

The detector controller 84 controls the operation of the radiation detector 33. The detector controller 84 makes the radiation detector 33 perform the storage operation in a case where the irradiation of the radiation R is started in radioscopy. The detector controller 84 makes the radiation detector 33 perform the reading operation in a case where the irradiation of the radiation R is stopped in radioscopy. With this, the radiographic image 45 (radioscopic image) is output from the radiation detector 33 for each irradiation of the radiation R.

The detector controller 84 makes the radiation detector 33 perform the detection operation at the detection interval DI in an off period of the foot switch 22 during which the irradiation of the radiation R is not performed. With this, the offset correction image 45O is output from the radiation detector 33.

The imaging instruction reception unit 85 receives an instruction to start and end radioscopy through the foot switch 22. The imaging instruction reception unit 85 outputs the received instruction to the radiation source controller 80, the distance measurement camera controller 82, and the detector controller 84.

Figure 12:
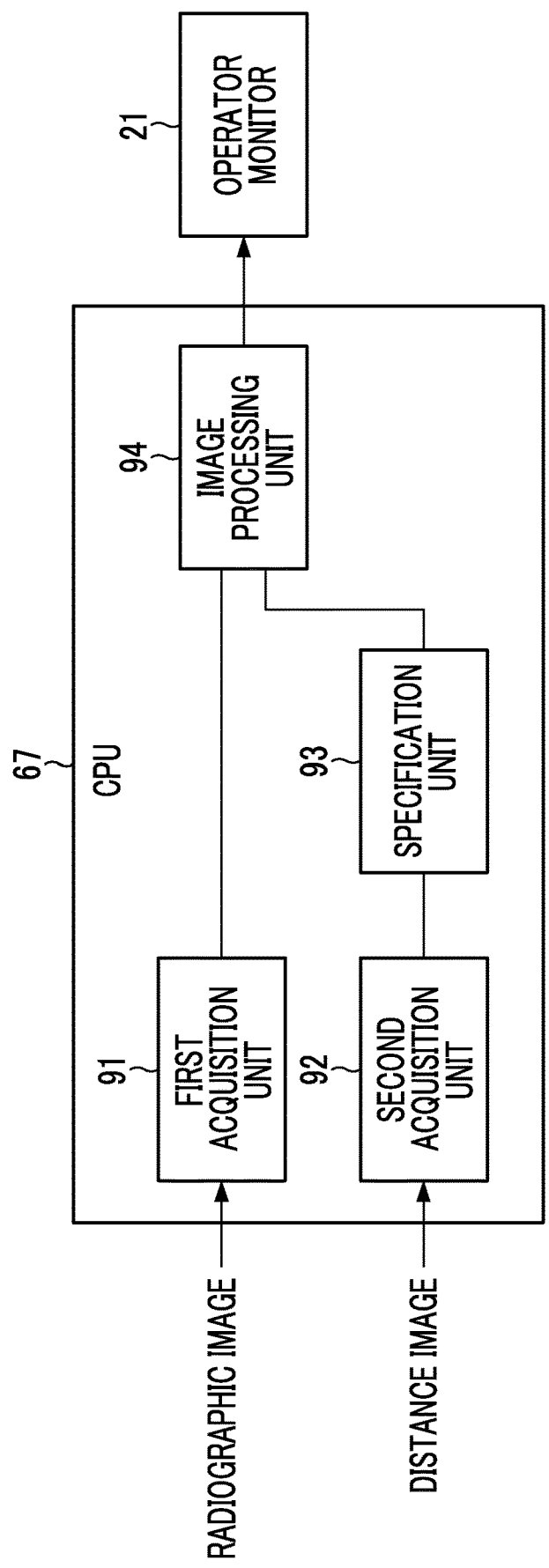
FIG. 12 is a block diagram showing an example of the functional configuration of a CPU that executes an image processing program.

FIG. 12 is a block diagram showing an example of the functional configuration of the CPU 67 that executes the image processing program 76. The CPU 67 functions as a first acquisition unit 91, a second acquisition unit 92, a specification unit 93, and an image processing unit 94 by executing the image processing program 76. The image processing program 76 is executed in parallel with the imaging control program 75.

The first acquisition unit 91 acquires the radiographic image 45 including an image of the patient P as a subject. The first acquisition unit 91 acquires a series of radiographic images 45 (radioscopic images) generated by radioscopy for continuously performing the irradiation of the radiation R from the radiation source 30 in real time. That is, the radiographic images 45 generated by the radiation detector 33 are transmitted to the console 11 instantly after generation, and are acquired by the first acquisition unit 91.

The second acquisition unit 92 acquires the distance image 55 including the image of the patient P imaged in real time before imaging of the radiographic images 45 acquired by the first acquisition unit 91. That is, the second acquisition unit 92 acquires the distance image 55 captured after positioning of the radiation source 30, the radiation detector 33, and the patient P is completed and at the time of non-irradiation of the radiation R. Accordingly, a timing at which the second acquisition unit 92 acquires the distance image 55 is earlier than a timing at which the first acquisition unit 91 acquires the radiographic images 45. Referring to FIG. 8, the second acquisition unit 92 acquires the distance image 55 surrounded by a two-dot chain line in the drawing and captured in the off period before the foot switch is brought into the on state, and the first acquisition unit 91 acquires the radiographic images 45 generated in an on period of the foot switch thereafter.

Figure 13:
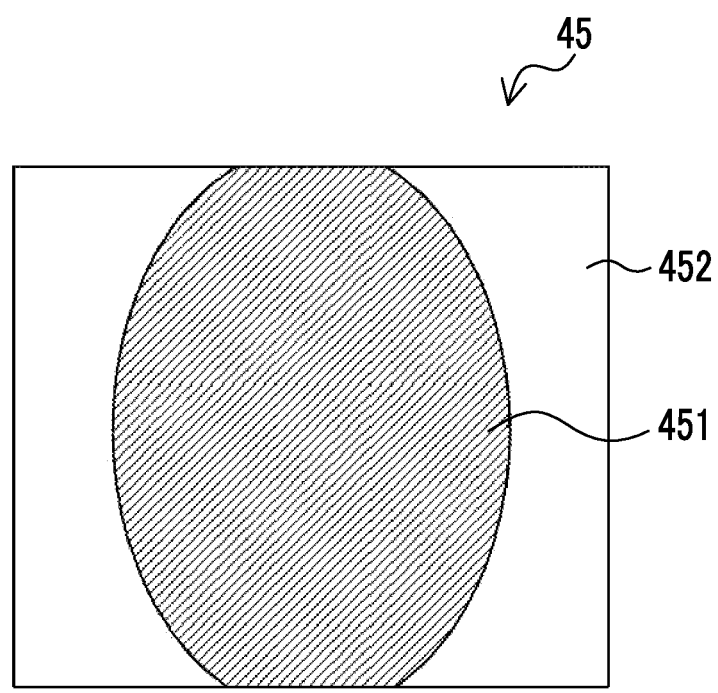
FIG. 13 is a diagram schematically showing a radiographic image.

The specification unit 93 executes processing (hereinafter, referred to as specification processing) of specifying a region (hereinafter, referred to as a subject region) in the radiographic image 45 acquired by the first acquisition unit 91 where the image of the patient P is formed, based on the distance image 55 acquired by the second acquisition unit 92. The specification unit 93 starts the above-described specification processing before the first acquisition unit 91 acquires the radiographic image 45. FIG. 13 is a diagram schematically showing the radiographic image 45. The radiographic image 45 includes a subject region 451 where an image of the patient P is formed with the irradiation of the radiation R to the radiation detector 33 through the patient P and a directly irradiated region 452 where the irradiation of the radiation R is performed directly to the radiation detector 33 without passing through the patient P. The specification unit 93 performs the specification of the subject region 451 in the radiographic image 45 based on the distance image 55, not the radiographic image 45. Hereinafter, details of the specification processing will be described.

As shown in FIG. 6, the distance image 55 includes image portions corresponding to the patient P and the imaging table 20. A distance between the distance measurement camera 32 and the patient P is different from a distance between the distance measurement camera 32 and the imaging table 20, and thus, the difference in distance is reflected in the pixel value of the distance image 55. Accordingly, it is possible to specify a region in the distance image 55 where the patient P is present. The specification unit 93 specifies a region where the distance indicated by the distance image 55 is within a predetermined range, as the region in the distance image 55 where the patient P is present. The above-described predetermined range is a range shorter than the distance between the distance measurement camera 32 and the imaging table 20.

A relative positional relationship between the radiographic image 45 and the distance image 55, that is, a pixel of the distance image 55 to which each pixel of the radiographic image 45 corresponds can be known by a preliminary experiment or the like. For example, it is possible to know a correspondence relationship between the pixels of the radiographic image 45 and the distance image 55 by comparing coordinate positions in the radiographic image 45 and the distance image 55 of images of a phantom included in the radiographic image 45 and the distance image 55 captured in a state in which the phantom is placed on the imaging table 20. Accordingly, it is possible to specify the subject region 451 in the radiographic image 45 from the region specified as the region in the distance image 55 where the patient P is present. The specification unit 93 specifies a region in the radiographic image 45 corresponding to the region specified as the region in the distance image 55 where the patient P is present, as the subject region 451 in the radiographic image 45 based on information indicating the relative positional relationship between the distance image 55 and the radiographic image 45 acquired in advance. The specification unit 93 performs the specification of the subject region 451 based on the distance image 55, not the radiographic image 45, and thus, can perform the specification of the subject region 451 before the acquisition of the radiographic image 45.

The image processing unit 94 executes image processing of enhancing the contrast of the subject region 451 specified by the specification unit 93 to the radiographic image 45 acquired by the first acquisition unit 91. Here, an upper section of FIG. 14 is an example of a histogram of the pixel values of the radiographic image 45. A lower section of FIG. 14 is a diagram showing an example of image processing by the image processing unit 94, and is a diagram showing an example of a relationship between a pixel value of the radiographic image 45 and a gradation value of a display image displayed on the operator monitor 21. Although FIG. 14 illustrates a case where the resolution of the gradation of the display image displayed on the operator monitor 21 is eight bits (minimum gradation value 0 and maximum gradation value 255), the present disclosure is not limited thereto.

Each pixel of the radiographic image 45 has a pixel value corresponding to a dose of radiation detected by the radiation detector 33. As shown in a histogram of the upper section of FIG. 14, the radiographic image 45 includes pixels having a pixel value corresponding to the subject region 451 and pixels having a pixel value corresponding to the directly irradiated region 452. The directly irradiated region 452 has a relatively high detection dose in the radiation detector 33, and the subject region 451 has a relatively low detection dose in the radiation detector 33.

In the lower section of FIG. 14, as indicated by a dotted line (no contrast enhancement), in a case where the gradation values 0 to 255 in the display image are allocated to a pixel value range including the pixel values of the subject region 451 and the pixel values of the directly irradiated region 452, for example, linearly (equally), a difference in brightness and darkness of the image portion of the subject region 451 is reduced. That is, in this case, the contrast of the subject region 451 in the radiographic image 45 decreases, and visibility is degraded.

To avoid the above-described problem, the image processing unit 94 executes image processing of enhancing the contrast of the subject region 451. Specifically, as indicated by a solid line in the lower section of FIG. 14, the image processing unit 94 allocates the gradation values 0 to 255 in the display image to the pixel value range of the subject region 451 in the radiographic image 45 specified by the specification unit 93. That is, the image processing unit 94 performs contrast adjustment of the display image displayed on the operator monitor 21 based on solely the pixel values of the subject region 451. The allocation of the gradation values 0 to 255 to the pixel value range of the subject region 451 may be performed such that the relationship between the pixel value and the gradation value is linear as illustrated in FIG. 14 or may be performed such that the relationship between the pixel value and the gradation value is nonlinear as illustrated in FIG. 15. The image processing unit 94 executes the image processing of enhancing the contrast of the subject region 451 to each of a series of radiographic images 45 acquired by the first acquisition unit 91. The image processing unit 94 sequentially outputs the image after the image processing. The image after the image processing is supplied to the operator monitor 21. With this, the radiographic image 45 subjected to the image processing of enhancing the contrast of the subject region 451 is displayed on the operator monitor 21.

The image processing unit 94 may execute offset correction processing on the radiographic image 45, in addition to the image processing of enhancing the contrast. The offset correction processing is processing for subtracting the offset correction image 45O output in a state in which the irradiation of the radiation R is not performed, from the radiographic image 45 output by radioscopy in units of pixels. In the offset correction processing, a latest offset correction image 45O surrounded by a frame of a two-dot chain line in FIG. 8 is used. The image processing unit 94 executes the offset correction processing to remove fixed pattern noise due to dark charge or the like from the radiographic image 45.

The distance measurement camera controller 82 makes the distance measurement camera 32 perform the imaging operation of the distance image 55 even at the time of non-irradiation of the radiation R after the foot switch 22 transits from the on state to the off state. For example, in orthopedic reduction, radioscopy is performed while changing the posture of the patient P multiple times. The irradiation of the radiation R is stopped once at a timing of changing the posture of the patient P. The distance measurement camera controller 82 makes the distance measurement camera 32 perform the imaging operation of the distance image 55 at the time of non-irradiation of the radiation R after the foot switch 22 transits from the on state to the off state, and thus, in a case where the posture of the whereby patient P is changed, the distance image 55 after the posture change is captured. That is, the distance image 55 is updated at the time of non-irradiation of the radiation R.

The second acquisition unit 92 acquires the updated distance image 55 captured after the foot switch 22 transits from the on state to the off state. The specification unit 93 performs the specification of the subject region 451 in the radiographic image 45 based on the updated distance image 55. With this, a specification result of the subject region 451 is updated. The image processing unit 94 executes the above-described image processing on the radiographic image 45 acquired by the first acquisition unit 91 after the acquisition of the updated distance image 55 based on the updated specification result of the subject region 451.

FIG. 16 is a flowchart showing an example of a flow of image processing that is executed by the CPU 67 executing the image processing program 76.

As shown in FIG. 8, prior to radioscopy, the imaging order corresponding to the imaging menu is selected by the operator OP, and accordingly, the irradiation conditions are set in the voltage generator 41 by the radiation source controller 80. The adjustment of the opening degree of the emission opening of the collimator 31 is performed by the collimator controller 81. Subsequently, positioning of the radiation source 30, the radiation detector 33, and the patient P is performed by the operator OP. After positioning is completed, for example, in a case where an execution instruction of imaging control processing is input through the input device 13, the imaging control program 75 is executed. The distance measurement camera controller 82 makes the distance measurement camera 32 perform the imaging operation of the distance image 55 in compliance with the imaging control program 75, and the CPU 67 executes the image processing program 76.

In Step ST20, as described above, the second acquisition unit 92 acquires the distance image 55 including the image of the patient P in real time at a timing before the foot switch 22 is brought into the on state by the operator OP, that is, before imaging of the radiographic image 45 after positioning of the radiation source 30, the radiation detector 33, and the patient P is completed.

In Step ST21, as described above, the specification unit 93 specifies the subject region 451 in the radiographic image 45 acquired in subsequent Step ST23 based on the distance image 55 acquired in Step ST20.

In Step ST22, the CPU 67 determines whether or not the foot switch 22 is depressed (on state). In a case where determination is made that the foot switch 22 is depressed (on state), the CPU 67 progresses the process to Step ST23. The irradiation of the radiation R is continuously performed from the radiation source 30 with the depression of the foot switch 22, and radioscopy is performed in the radiation detector 33.

In Step ST23, the first acquisition unit 91 acquires the radiographic images 45 including the image of the patient P. The first acquisition unit 91 acquires a series of radiographic images 45 (radioscopic images) generated by radioscopy in real time as described above.

In Step ST24, the image processing unit 94 executes the image processing of enhancing the contrast of the subject region 451 specified in Step ST21 to each of a series of radiographic images 45 acquired in Step ST23 as described above. The image processing unit 94 sequentially outputs the image after the image processing. With this, the radiographic image 45 subjected to the image processing of enhancing the contrast of the subject region 451 is displayed on the operator monitor 21.

In Step ST25, the CPU 67 determines whether or not the depression of the foot switch 22 is released (off state). In a case where the depression of the foot switch 22 is continued, the CPU 67 returns the process to Step ST23. That is, in this case, the image processing of enhancing the contrast of the subject region 451 in the radiographic images 45 continuously generated in radioscopy is consecutively executed. In a case where determination is made that the depression of the foot switch 22 is released, the CPU 67 progresses the process to Step ST26.

In Step ST26, the CPU 67 determines whether or not an end instruction of radioscopy is input. The end instruction of radioscopy can be performed, for example, through the input device 13. In a case where determination is made that the end instruction of radioscopy is not input, the CPU 67 returns the process to Step ST20. In this case, it is assumed that the posture of the patient P is changed and the distance image 55 after the posture change is captured. The second acquisition unit 92 acquires the updated distance image 55. The specification unit 93 updates the specification result of the subject region 451 in the radiographic image 45 based on the updated distance image 55. The image processing unit 94 executes the image processing of enhancing the contrast of the subject region 451 to each of a series of radiographic images 45 acquired with the re-depression of the foot switch 22 based on the updated specification result. In a case where determination is made that the end instruction of radioscopy is input, the CPU 67 ends the routine.

As described above, with the console 11 functioning as the image processing apparatus according to the embodiment of the technique of the present disclosure, the specification unit 93 specifies the subject region in the radiographic image 45 based on the distance image 55, and the image processing unit 94 executes the image processing of enhancing the contrast of the subject region 451 specified by the specification unit 93 to the radiographic image 45. With this, even though the radiographic image 45 includes the directly irradiated region 452, it is possible to avoid a decrease in contrast in the subject region 451 as affected by the pixel value in the directly irradiated region 452.

Here, FIG. 17 is a timing chart showing an example of a flow of each kind of processing that is executed in a case of enhancing the contrast of the subject region 451 in each of a case (an upper section of FIG. 17) where the subject region 451 is specified based on the distance image 55 captured before imaging of the radiographic image 45 and a case (a lower section of FIG. 17) where the subject region 451 is specified based on the radiographic image 45 subjected to the image processing. The upper section of FIG. 17 is a timing chart regarding the image processing according to the embodiment of the technique of the present disclosure, and the lower section of FIG. 17 is a timing chart regarding image processing according to a comparative example.

As shown in the lower section of FIG. 17, in a case of the image processing according to the comparative example where the subject region 451 is specified based on the radiographic image 45 subjected to the image processing, the specification of the subject region 451 has to be performed after the acquisition of the radiographic image 45. On the other hand, as shown in the upper section of FIG. 17, with the image processing apparatus according to the embodiment of the technique of the present disclosure, the specification unit 93 performs the specification of the subject region 451 based on the distance image 55 captured before imaging of the radiographic image 45, and thus, it is possible to perform the specification of the subject region 451 independently of the imaging processing and the acquisition processing of the radiographic image 45. With this, it is possible to reduce a time lag TL from an imaging start time of the radiographic image 45 (a time when the foot switch 22 is depressed) until the image after image processing is output, compared to the image processing according to the comparative example where the subject region 451 is specified based on the radiographic image 45 subjected to the image processing. That is, with the console 11 functioning as the image processing apparatus according to the embodiment of the technique of the present disclosure, it is possible to increase the visibility of a radiographic image while ensuring a real time property of image display.

In the embodiment, although the distance measurement camera 32 using the TOF system is exemplified as a unit that acquires the distance image 55, the present disclosure is not limited thereto. As the unit that acquires the distance image 55, a stereo camera that measures a distance to an object from an image captured with two cameras having parallax may be used. Alternatively, an ultrasound sensor that emits an ultrasonic wave from an ultrasound transducer to measure a distance to an object based on an ultrasound echo reflected from the object may be used.

In the embodiment, although the distance measurement camera 32 is exemplified as a unit that specifies the subject region 451, the present disclosure is not limited thereto. As the unit that specifies the subject region 451, a general visible light camera can be used. In a case where the visible light camera is used, the subject region 451 can be specified from a visible light image captured by the visible light camera using a known image recognition technique. As the distance image 55 is used to specify the subject region 451, it is possible to perform the specification of the subject region 451 in a short time compared to a case where the visible light image is used. Accordingly, it is preferable that the distance image 55 is used in the specification of the subject region 451.

In the embodiment, although the timing at which the radiation detector 33 outputs the offset correction image 45O is exemplified as the timing at which the distance measurement camera 32 is made to capture the distance image 55, the present disclosure is not limited to the aspect. The distance measurement camera 32 may be made to capture the distance image 55 simply while the depression of the foot switch 22 is released.

Second Embodiment

A radioscopy apparatus 10 according to a second embodiment of the technique of the present disclosure performs tomosynthesis imaging in addition to radioscopy. As shown in FIG. 18, tomosynthesis imaging is imaging where the radiation source 30 is sequentially moved to a plurality of irradiation positions IP arranged at equal intervals along the longitudinal direction of the imaging table 20, the irradiation of the radiation R is performed from a plurality of focuses F corresponding to the respective irradiation positions IP to the radiation detector 33, and the radiographic image 45 (hereinafter, referred to as a projection image 45P) is output from the radiation detector 33 each time. In tomosynthesis imaging, the radiation detector 33 is placed at the center of the irradiation position IP. FIG. 18 shows an example of tomosynthesis imaging where the irradiation of the radiation R is performed from 15 focuses F1 to F15 corresponding to 15 irradiation positions IP1 to IP15 centering on an irradiation position IP8, and 15 projection images 45P are obtained.

As shown in FIG. 19, the CPU 67 of the console 11 reconfigures tomographic images 45T corresponding to tomographic planes TF1 to TFN of the patient P from the projection images 45P obtained through tomosynthesis imaging shown in FIG. 18 using a known method, such as a filtered back projection method. The CPU 67 reconfigures the tomographic image 45T with a slice thickness SLT set in advance and outputs the tomographic image 45T. With this, the tomographic image 45T is displayed on the operator monitor 21.

In the embodiment, the CPU 67 of the console 11 derives a body thickness of the patient P based on the distance image 55. In a case where a distance between the radiation source 30 (distance measurement camera 32) and the surface of the imaging table 20 is D1, and a distance between the radiation source 30 (distance measurement camera 32) and a shortest point of the body surface of the patient P is D2, a body thickness BT of the patient P can be calculated by Expression (1) described below.

$$BT = D1 - D2 \qquad (1)$$

As described above, the distance D1 between the radiation source 30 and the surface of the imaging table 20 is invariable. For this reason, it is possible to derive the body thickness BT of the patient P by deriving the distance D2 between the radiation source 30 and the shortest point of the body surface of the patient P from the distance image 55.

The CPU 67 of the console 11 performs the derivation of the distance D2 as follows, for example. First, the distance D1 is invariable and known, and thus, a region of the distance image 55 having a distance less than the distance D1 as a pixel value is recognized as a region where the patient P is present. Next, a point at the shortest distance in the recognized region where the patient P is present, that is, a shortest point is searched, and a pixel value of the searched shortest point is derived as the distance D2.

As shown in FIG. 20, the CPU 67 sets the slice thickness SLT corresponding to the body thickness BT of the patient P derived from the distance image 55 with reference to a slice thickness table 500 (Step ST500). In the slice thickness table 500, the slice thickness SLT of a greater value is registered as the body thickness is thicker. The slice thickness table 500 is stored in the storage device 65.

After the slice thickness SLT is set, tomosynthesis imaging shown in FIG. 18 is performed (Step ST510). With this, a plurality of projection image 45P corresponding to the respective irradiation positions IP are obtained. Then, as shown in FIG. 20, the tomographic image 45T is reconfigured from the projection image 45P with the slice thickness SLT set by the CPU 67 (Step ST520). The reconfigured tomographic image 45T is displayed on the operator monitor 21 under the control of the CPU 67 (Step ST530).

FIG. 21 is a flowchart showing a procedure in the related art as a comparative example. In the related art, the operator OP manually sets a slice thickness SLT through the input device 13 based on a body thickness BT of a visible aspect of the patient P (Step ST1000). For this reason, the operator OP determines whether or not the manually set slice thickness SLT is appropriate based on the tomographic image 45T displayed on the operator monitor 21 (Step ST1100). Then, in a case where the manually set slice thickness SLT is not appropriate (in Step ST1100, NO), the operator OP resets the slice thickness SLT (Step ST1200), and the processing of Steps ST520 and ST530 is repeated. A time of about several minutes is needed in reconfiguring the tomographic image 45T from the projection image 45P after the slice thickness SLT is reset. Therefore, in the related art, there is a case where a time is needed to obtain a tomographic image 45T at a desired slice thickness SLT.

In contrast, in the second embodiment, as shown in FIG. 20, the slice thickness SLT is automatically set depending on the body thickness BT of the patient P converted from the distance image 55. Accordingly, a lot of labor is not needed to reset the slice thickness SLT unlike the related art, and a lot of time is not needed until the tomographic image 45T of a desired slice thickness SLT is obtained.

As the hardware structures of processing units that execute various kinds of processing, such as the radiation source controller 80, the collimator controller 81, the distance measurement camera controller 82, the detector controller 84, the imaging instruction reception unit 85, the first acquisition unit 91, the second acquisition unit 92, the specification unit 93, and the image processing unit 94, various processors described below can be used. Various processors include at least one of a programmable logic device (PLD) that is a processor capable of changing a circuit configuration after manufacture, such as the FPGA, a dedicated electric circuit that is a processor having a circuit configuration dedicatedly designed for executing specific processing, such as an application specific integrated circuit (ASIC), or the like, in addition to the CPU 67 that is a general-purpose processor executing software to function as various processing units.

One processing unit may be configured of one of various processors described above or may be configured of a combination of two or more processors (for example, a combination of a plurality of FPGAs and/or a combination of a CPU and an FPGA) of the same type or different types. A plurality of processing units may be configured of one processor.

As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, as the hardware structure of various processors, more specifically, an electric circuit (circuitry), in which circuit elements, such as semiconductor elements, are combined, can be used.

The technique of the present disclosure can also be appropriately combined with at least one of various embodiments or various modification examples described above. The technique of the present disclosure is not limited to the above-described embodiments, and various configurations can be of course employed without departing from the spirit and scope of the technique of the present disclosure. In addition to the program, the technique of the present disclosure extends to a storage medium that stores the program in a non-transitory manner.

The content of the above description and the content of the drawings are detailed description of portions according to the technique of the present disclosure, and are merely examples of the technique of the present disclosure. For example, the above description relating to configuration, function, operation, and advantageous effects is description relating to examples of configuration, function, operation, and advantageous effects of the portions according to the technique of the present disclosure. Thus, it is needless to say that unnecessary portions may be deleted, new elements may be added, or replacement may be made to the content of the above description and the content of the drawings without departing from the gist of the technique of the present disclosure. Furthermore, to avoid confusion and to facilitate understanding of the portions according to the technique of the present disclosure, description relating to common technical knowledge and the like that does not require particular description to enable implementation of the technique of the present disclosure is omitted from the content of the above description and the content of the drawings.

What is claimed is:

1. An image processing apparatus comprising:
at least one processor,
wherein the processor is configured to execute processing of
acquiring a plurality of first images that configure a video, and are radiographic images including an image of a subject, the plurality of the first images continuously captured by radioscopy by continuously irradiating the subject with radiation,
acquiring a second image different from the radiographic image including the image of the subject before acquiring the plurality of first images,
specifying a subject region as a region where the image of the subject is formed in the plurality of first images, based on the second image, and
executing image processing of enhancing contrast of the specified subject region on the plurality of first images and continuously outputting the plurality of contrast enhanced first images as the video, after the image processing,
wherein the processor is further configured to
acquire an updated second image at the time of non-irradiation of the radiation after the plurality of first images is acquired,
update a specification result of the subject region in the plurality of first images based on the updated second image, and
execute the image processing on the plurality of first images acquired after the acquisition of the updated second image based on the updated specification result.

2. The image processing apparatus according to claim 1, wherein the second image is a distance image indicating a distance to the subject.

3. The image processing apparatus according to claim 2, wherein the processor is configured to specify a region where the distance indicated by the distance image is within a predetermined range, as a region where the subject is present, and specify a region in the first image corresponding to the region specified as the region in the distance image where the subject is present, as the subject region in the plurality of first images.

4. The image processing apparatus according to claim 2, wherein the distance image is generated by a distance measurement camera that generates a distance image representing a distance to a surface of an object using a time-of-flight system.

5. A radioscopy system comprising:
the image processing apparatus according to claim 1;
a radiation detector that captures the plurality of first images;
a radiation source that performs irradiation of radiation for use in imaging the plurality of first images; and
an imaging apparatus that captures the second image.

6. The radioscopy system according to claim 5, wherein the imaging apparatus is a distance measurement camera that generates a distance image representing a distance to a surface of an object using a time-of-flight system.

7. A non-transitory computer-readable storage medium storing an image processing program causing a processor in an image processing apparatus to execute processing of
- acquiring a plurality of first images that configure a video, and are radiographic images including an image of a subject, the plurality of the first images continuously captured by radioscopy by continuously irradiating the subject with radiation,
- acquiring a second image different from the radiographic image including the image of the subject before acquiring the plurality of first images,
- specifying a subject region as a region where the image of the subject is formed in the plurality of first images, based on the second image, and
- executing image processing of enhancing contrast of the specified subject region on the plurality of first images and continuously outputting the plurality of contrast enhanced first images as the video, after the image processing, wherein the processor is further configured to
- acquire an updated second image at the time of non-irradiation of the radiation after the plurality of first images is acquired,
- update a specification result of the subject region in the plurality of first images based on the updated second image, and
- execute the image processing on the plurality of first images acquired after the acquisition of the updated second image based on the updated specification result.

8. An image processing method, wherein a processor in an image processing apparatus executes processing of
- acquiring a plurality of first images that configure a video, and are radiographic images including an image of a subject, the plurality of the first images continuously captured by radioscopy by continuously irradiating the subject with radiation,
- acquiring a second image different from the radiographic image including the image of the subject before acquiring the plurality of first images,
- specifying a subject region as a region where the image of the subject is formed in the plurality of first images, based on the second image, and
- executing image processing of enhancing contrast of the specified subject region on the plurality of first images and continuously outputting the plurality of contrast enhanced first images as the video, after the image processing, wherein the processor is further configured to
- acquire an updated second image at the time of non-irradiation of the radiation after the plurality of first images is acquired,
- update a specification result of the subject region in the plurality of first images based on the updated second image, and
- execute the image processing on the plurality of first images acquired after the acquisition of the updated second image based on the updated specification result.

* * * * *